United States Patent
Rangan et al.

(10) Patent No.: US 10,272,172 B2
(45) Date of Patent: *Apr. 30, 2019

(54) MULTIFUNCTIONAL TRANSDERMAL DRESSING FOR WOUNDS

(71) Applicant: MATERIALS MODIFICATION INC., Fairfax, VA (US)

(72) Inventors: Krishnaswamy Kasthuri Rangan, Fairfax, VA (US); Tirumalai Srinivas Sudarshan, Vienna, VA (US)

(73) Assignee: MATERIALS MODIFICATION INC, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,122

(22) Filed: Nov. 7, 2016

(65) Prior Publication Data

US 2018/0043049 A1    Feb. 15, 2018

Related U.S. Application Data

(63) Continuation-in-part of application No. 14/210,082, filed on Mar. 13, 2014.

(60) Provisional application No. 62/253,503, filed on Nov. 10, 2015, provisional application No. 61/794,420, filed on Mar. 15, 2013.

(51) Int. Cl.
| | | |
|---|---|---|
| A61L 15/18 | (2006.01) | |
| A61L 15/44 | (2006.01) | |
| A61K 33/38 | (2006.01) | |
| A61K 31/167 | (2006.01) | |
| A61F 13/00 | (2006.01) | |
| A61K 31/4468 | (2006.01) | |
| A61L 15/46 | (2006.01) | |

(52) U.S. Cl.
CPC ........ *A61L 15/18* (2013.01); *A61F 13/00063* (2013.01); *A61K 31/167* (2013.01); *A61K 31/4468* (2013.01); *A61K 33/38* (2013.01); *A61L 15/44* (2013.01); *A61L 15/46* (2013.01); *A61F 2013/00157* (2013.01); *A61L 2300/402* (2013.01); *A61L 2300/404* (2013.01)

(58) Field of Classification Search
None
See application file for complete search history.

(56) References Cited

U.S. PATENT DOCUMENTS

| | | | | |
|---|---|---|---|---|
| 2012/0183588 A1* | 7/2012 | Supamahitorn | ........ | A01N 25/04 424/401 |
| 2014/0276484 A1* | 9/2014 | Mukhopadhyay | ...... | A61L 15/18 604/307 |

* cited by examiner

*Primary Examiner* — Jessica Worsham
(74) *Attorney, Agent, or Firm* — Jyoti C. Iyer

(57) ABSTRACT

A multifunctional polymer-free clay products having a clay, a zwitterion, a silver compound, and, an analgesic. The multifunctional polymer-free clay product provides antimicrobial and pain relieving properties. Method of treatment of burns using the multifunctional polymer-free clay product having antimicrobial and pain relieving properties. Methods of preparing multifunctional polymer-free clay products having a clay, a zwitterion, a silver compound, and, an analgesic.

6 Claims, 14 Drawing Sheets

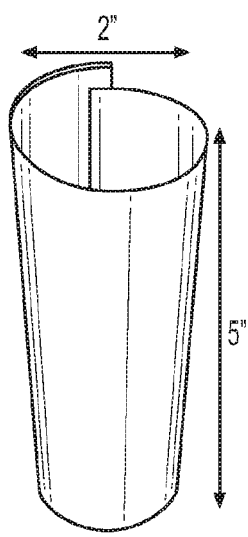 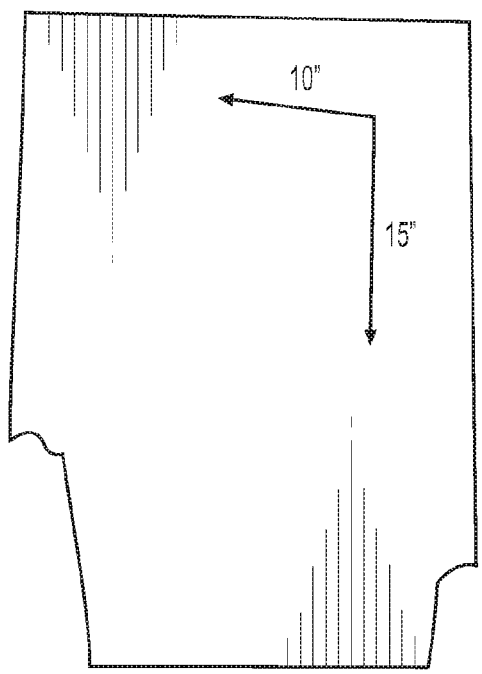
FIG. 1A  FIG. 1B

MULTIFUNCTIONAL TRANSDERMAL DRESSING FOR WOUNDS

This Application claims the benefit of U.S. Appl. Ser. No. 62/253,503, filed Nov. 10, 2015, and, is a continuation-in-part of co-pending U.S. application Ser. No. 14/210,082, filed Mar. 13, 2014, which claims benefit of U.S. Appl. Ser. No. 61/794,420 filed Mar. 15, 2013, which are incorporated in entirety by reference.

STATEMENT REGARDING FEDERALLY SPONSORED RESEARCH OR DEVELOPMENT

This work was supported by the Government of the United States of America under Contract No. W81XWH-14-C-0130, awarded by the United States Department of Defense. The Government of the United States of America has certain rights in this invention.

FIELD

This disclosure relates to a multifunctional bandage for wounds. Disclosure provides a bandage based on claymat with antimicrobial property. A mat based on silver containing claymat with analgesic property is provided. A bandage based on claymat with both antimicrobial and analgesic properties in the same product is provided. A transdermal delivery product based on claymat for analgesics is provided. A transdermal delivery product based on claymat for local anesthetic is provided.

BACKGROUND

In this section, we discuss several aspects of related work, including background and conventional technologies.

Burns are among the most painful and debilitating battlefield wounds faced by the US warfighter. Burn wounds turn deadly when infection sets in. Since military operations began in Iraq in March 2003, hundreds of US military personnel have sustained burn injuries from explosions and other implements of war such as IED's [E. M. Renz et al. Long Range Transport of War-Related Burn Casualties, J Trauma. 64, S136-S145 (2008)], Acute burn injury pain is a source of immense suffering, and it has been linked to debilitating chronic pain and stress-related disorders. Severe pain is felt during acute treatment and rehabilitation, especially during dressing changes, debridement's, and skin grafting, and continues through long-term follow-up. The backbone of burn analgesia is opioid therapy, typically administered via oral or parenteral routes. The systemic use of opioid medications in burn patients is complicated by the side effects such as tolerance, hyperalgesia, hemodynamic instability, respiratory depression, and dependence. Therefore, besides the systemic administration of analgesics, attempts have been made to control the pain locally using topical analgesics which have shown encouraging results [T. Long, T. Cathers, R. Twillman, T. O'Donnell, N. Garrigues, T. Jones, Morphine-Infused Silver Sulfadiazine Cream for Burn Analgesia: A Pilot Study, Journal of Burn Care & Rehabilitation, 22, 118-123, (2001)]. Such topical dressings can be used to protect the burn wound from infection and thereby aid in wound healing if antimicrobial properties can be imparted to them. Topical antimicrobial-analgesic dressings can also be used to treat major irritation/pain problems such as abrasions, friction irritations and pressure sores (blisters).

Fentanyl, an opioid analgesic was incorporated into an antimicrobial wound dressing based on silver containing clay mats. This fentanyl-loaded silver containing clay mat can provide controlled delivery of analgesic drugs to wounds while assisting in wound healing with its antimicrobial properties. Silver containing clay mats were prepared and evaluated in vitro for their antimicrobial activity and their ability to provide controlled release of fentanyl. The antimicrobial properties of both silver containing claymats without Fentanyl and with Fentanyl loading were demonstrated using Kirby-Bauer assay tests. After optimizing the kinetics of the opioid delivery in vitro, the efficacy of silver containing claymats with fentanyl as a topical analgesic dressing was tested using a standard hot plate animal model. The Hot Plate test, in a rodent model, clearly demonstrated the ability of silver containing claymats with fentanyl patches to elicit cutaneous antinociception activity due to regional delivery of subtherapeutic doses of fentanyl. Pain and Infection are the two major complications associated with second-degree burn injuries. Silver containing claymats with fentanyl mat is a single patch device that can be used to alleviate pain and prevent infection in burn injuries.

Burn Injury Pain and Action of Analgesics

The description of the pain pathway as provided by Kehlet et al. [H. Kehlet J. B. Dahl, The value of "multimodal" or "balanced analgesia" in postoperative pain treatment. Anesth. Analg; 77,1049 (1993)] and Gottschalk et al. [H. Kehlet, J. B. Dahl, The value of "multimodal" or "balanced analgesia" in postoperative pain treatment, Anesth Analg; 77,1049 (1993)] is as follows: "Both the peripheral and the central nervous systems (CNS) are involved in the perception of pain. The transmission of burn wound pain stimuli begins with peripheral nociceptors. The pain message from the nociceptors is transmitted via A-delta and C fibers to the dorsal horn of the spinal cord [P. Richardson, L. Mustard, The management of pains in the burns unit, Burns, 35, 921-936, (2009)]. The sensitivity of nociceptors is further enhanced by many tissue factors and inflammatory chemicals released in the course of tissue injury." Therefore, the baseline pain management must include treatment of both nociceptive and neuropathic components. Nociceptive receptors can be controlled by local medication while neuropathic parts will require systemic administration of analgesics.

Action of Topical Analgesics

Treatment for reducing pain involves the use of common and opioid analgesics, nonsteroidal anti-inflammatory drugs (NSAIDs) and adjuvant analgesics [M. P. Flores, A. P. Rocha de Castro, J. S. Nascimento, Topical Analgesics, Revista Brasileira de Annesesiologie, 62, 244-252, (2012)]. Pharmacologically, it is known that the main mechanism of analgesics is to act at specific sites located in the CNS and periphery. This observation led the topical administration of pain reliever drags such as NSAID's, local anesthetics, capsaicin, tricyclic antidepressants, ketamine, clonidine, opioids, and cannabinoids. For example, fentanyl transdermal patches are used to treat chronic pain from cancer or in the post-operative setting [M. Lane, The transdermal delivery of fentanyl, European Journal of Pharmaceutics and Biopharmaceutics, 84, 449-455, (2013)]. The topical application of these dregs allows high concentrations in peripheral effector sites. Thus, undesirable side effects are less likely to occur compared to delivering these drugs systemically.

Human skin consists of three main layers: the epidermis, dermis, and hypodermis. An applied drug most traverse these structural layers, encountering several lipophilic and hydrophilic domains on the way to the dermis where absorption into systemic circulation is rapid due to large capillary beds [L. Margetts, R. Sawyer, Transdermal Drug Delivery: Principles and Opioid Therapy, Continuing Education in Anesthesia, Critical Care & Pain, 7, 171-176, (2007)]. Therefore, the action of transdermal supply of analgesic will take more time than systemic administration of the same drug. For example, after initial application, fentanyl concentrations in blood increase gradually, generally leveling off between 12 and 24 h. In the case of a burn injury, the drug absorption rate through the skin will also be affected by various other factors such as the degree of burn, thickness of skin and body temperature. The conventional wisdom is that even though opioid drugs are applied locally on the skin, the main analgesic action of opioids occurs only in the spinal cord. This will require the drug to be absorbed into the blood and travel from the skin surface to the spinal cord. The treatment of severe pain with opioids has thus far been limited by their unwanted central side effects.

Recent pioneering work by Stein et al. and others promises the possibility of opioid analgesic action outside the CNS. Recently, opioid receptors have been identified on peripheral processes of sensory neurons. Opioids can attenuate the excitability of peripheral nociceptor terminals, reduce the conduction of pain signals and the release of excitatory proinflammatory neuropeptides (substance P, calcitonin gene-related peptide) from peripheral sensory nerve endings. In other words, areas with injury or burns generate chemical substances that irritate nerve endings even more and cause pain. Opioids apparently decrease the formation of these substances and decrease the response of nerve fibers to these substances. The modulating effect of fentanyl on the nerve endings can be translated into a clinically significant effect on pain relief.

Clays as a Drug Delivery Medium

Fentanyl loaded silver containing claymat patches were prepared using montmorillonite clay as the matrix for Fentanyl. Clays are common ingredients in pharmaceutical products. Clay minerals are naturally occurring inorganic cationic exchangers that can undergo ion exchange with basic drugs in solution. In addition to ion-exchange, organic molecules can bond to clays via physical adsorption and ion-dipole interactions of acidic and non-ionized molecules. For example, Wai and Banker demonstrated the loading of alkaloids in montmorillonite clay [K. N. Wai, G. S. Banker, Some physicochemical properties of the montmorillonites. J. Pharm. Sci. 55, 1215-1220 (1966)]. One major advantage of using clays to deliver drugs compared to other delivery systems is the very low risk of 'dose dumping'. Common topical medical dressings such as gauze, membranes and textiles can be subjected to dose dumping easily due to external forces. Thus, a material of high chemical and mechanical resistance is required to develop a safe, high potency opioid transdermal drug delivery vehicle [C. Aguzzi, P. Cerezo, C. Viseras, C. Caramella, Use of clays as drug delivery systems: Possibilities and limitations, Applied Clay Science, 36, 22-36, (2007)]. Clays are the most optimum storage and delivery systems for analgesics because of their mechanical and chemical stability. Fentanyl has been loaded into a metakaolin clay, which provided a mechanically strong sustained drug release medium [K. N. Wai, G. S. Banker, Some physicochemical properties of the montmorillonites. J. Pharm. Sci. 55, 1215-1220 (1966)]. The multifunctional patch can be used in skin graft patients, for pain management at the skin donor site.

The transdermal absorption of opioid drugs like fentanyl may take up to 8-12 h to take action. However, the injured patient requires the drugs to provide immediate relief. One approach is to use local anesthetics such as Lidocaine base or Loperamide base instead of Fentanyl or in combination with Fentanyl.

Lidocaine hydrochloride molecules strongly bound to the claymat through an intercalation process. For example, Kevadiya et al. intercalated Lidocaine hydrochloride into montmorillonite clay by ion exchange and investigated the controlled drug release [B. D. Kevadiya, G. V. Joshi, H. M. Mody, H. C. Bajaj, Biopolymer-clay hydrogel composites as drug carrier: Host-guest intercalation and in vitro release study of lidocaine hydrochloride, Applied Clay Science, 52, 364-367 (2011)]. The in vitro release experiments showed that lidocaine release from montmorillonite clay was controlled by pH of the extracting liquid medium. Lidocaine was released faster at alkaline or neutral pH. Abdel-Mohsen et al. studied the ionic state of lidocaine as a function of pH [M. G. Abdel-Mohsen, H. A. Mohamed, H. M. A. Wadood, Study of the effect of montmorillonite and Florite on the dissociation constant, release and local anesthetic activity of lidocaine, STP Pharma Sciences, 4, 295-300 (2001)]. They also demonstrated that Lidocaine hydrochloride release in water is affected by the pH indicating the interaction of lidocaine cations with the clay surface. Conditions for transdermal drug delivery is different from in vivo drug delivery or in vivo drug release. The transdermal delivery of drugs occurs in a dry state without a major amount of fluids. In comparison, drug delivery through oral administration occur in the presence of a large amount of bodily fluids and strongly depends on the pH of the medium.

The availability of fluids on the skin surface to extract the drug from the drug delivery transdermal patches is very small or even absent on dry skins. Therefore, the transdermal mat should allow free mobility of the drug through the patch. This flow will be restricted if the polymers are used in the preparation of claymats.

The ammonium (+NH— and +N($C_2H_5$)$_2$—) groups on lidocaine hydrochloride interact strongly with the clay surface. No leaching of lidocaine hydrochloride was from the mats observed due to the strong binding of lidocaine hydrochloride with the claymat and silver containing claymat samples. Therefore, it was decided to use lidocaine base instead of lidocaine hydrochloride. This resulted in an increase in the release of lidocaine base from the claymat and silver containing claymat samples during the drug release testing.

SUMMARY

The disclosed teachings provide making of a pain relieving device based on clay mat. The disclosure provides a device based on clay mats with combined antimicrobial and pain relieving properties. The disclosure provides clay mat loaded with silver and analgesics.

The disclosed teachings provide making of a pain relieving device based on clay mat. The disclosure provides a device based on clay mats with combined antimicrobial and pain relieving properties. The disclosure provides clay mat loaded with an antimicrobial agent and analgesics. The disclosure provides clay mat loaded with silver and fentanyl. Some embodiments provide a multifunctional topical wound dressing capable of both antimicrobial action while delivering pain medication.

Some embodiments provide a multifunctional polymer-free clay product having clay, a zwitterion, an antimicrobial agent, and, an analgesic. The multifunctional polymer-free clay product provides antimicrobial and pain relieving properties. The clay can be montmorillonite, kaolinite, smectite, and bentonite. The antimicrobial agent can be silver ion, copper, silver-containing compounds, or, copper containing compounds. The zwitterion can be betaine, betaine hydrochloride, choline chloride, 3-Benzyl-5-(2-hydroxymethyl)-4-methylthiazolium chloride, 3-Benzyl-5-(2-hydroxymethyl)4-methylthiazolium bromide, 3-Benzyl-5-(2-hydroxymethyl)-4-methylthiazolium fluoride, [2-(Methacryloyloxy)ethyl]dimethyl-(3-sulfopropyl) ammonium hydroxide, [2-(Methacryloyloxy)ethyl]dimethyl-(3-sulfopropyl) ammonium chloride and 3-Benzyl-5-(2-hydroxymethyl)-4-methylthiazolium iodide. The analgesic can be opioid analgesics, nonsteroidal anti-inflammatory drugs (NSAIDs) and adjuvant analgesics, capsaicin, clonidine, ketamine, Morphine, fentanyl, Buprenorphine, fentanyl base, lidocaine base, loperamide base, cannabinoids, and combinations thereof. The thickness of the multifunctional polymer-free clay product ranges from about 1 micrometer to about 500 micrometers. In some embodiments, the thickness of the multifunctional polymer-free clay product ranges from about 1 micrometer to about 100 micrometers. The polymer-free clay product achieves a bending radius of curvature ranging from about 0.4 millimeters to about 10 centimeters. The polymer-free clay product can have greater than 50 percent absorption of visible light. The polymer-free clay product does not incorporate a polymer. Some embodiments provide a multifunctional dressing having a multifunctional polymer-free clay product.

Some embodiments provide a method of treating burns by administering a multifunctional polymer-free clay product having antimicrobial and pain relieving properties.

Some embodiments provide a method of preparing a multifunctional polymer-free clay product having an antimicrobial agent and an analgesic. The method includes mixing clay, an antimicrobial agent, and water to form a first clay slurry. Washing the first clay slurry with water to obtain a washed second clay slurry. Next, adding a zwitterion and water to the washed second slurry to obtain a third clay slurry. Then, casting the third clay slurry onto a substrate to obtain a first dried product. Then adding drops of an analgesic in a non-aqueous solvent onto the first dried product to obtain a resultant product. Then drying the resultant product to obtain a second dried product. Then separating the second dried from the substrate. The second dried product is the multifunctional polymer-free clay product. The multifunctional polymer-free clay product provides both antimicrobial and pain relieving properties. The antimicrobial in the multifunctional polymer-free clay product can be silver ion, copper, silver-containing compounds, and, copper containing compounds. In some embodiments, the silver compound is silver nitrate. The analgesic can be fentanyl base, lidocaine base, loperamide base, and combinations thereof. The substrate can be a silicone sheet, fabric, and a glass surface. The clay can be montmorillonite, kaolinite, smectite, and bentonite. The zwitterion can be betaine, betaine hydrochloride, choline chloride, 3-Benzyl-5-(2-hydroxymethyl)-4-methylthiazolium chloride, 3-Benzyl-5-(2-hydroxymethyl)-4-methylthiazolium bromide, 3-Benzyl-5-(2-hydroxymethyl)-4-methylthiazolium fluoride, [2-(Methacryloyloxy)ethyl]dimethyl-(3-sulfopropyl) ammonium hydroxide, [2-(Methacryloyloxy)ethyl]dimethyl-(3-sulfopropyl) ammonium chloride and 3-Benzyl-5-(2-hydroxymethyl)-4-methylthiazolium iodide.

In another embodiment of the method of preparing a multifunctional polymer-free clay product having an antimicrobial and an analgesic, the method includes mixing clay, an antimicrobial agent, and water to form a first clay slurry. Then washing the first slurry with water to obtain a washed second clay slurry. Then adding a mixture of water and a non-aqueous solvent containing betaine and an analgesic to the washed second slurry to obtain a third clay slurry. Next, casting the third clay slurry onto a substrate to obtain a dried product. Next, separating the dried product from the substrate to obtain a separated dried product. The separated dried product is the multifunctional polymer-free clay product, which provides antimicrobial and pain relieving properties. The antimicrobial agent can be silver ion, copper, silver-containing compounds, or, copper containing compounds. In some embodiments, the silver compound is silver nitrate. The analgesic can be fentanyl base, lidocaine base, loperamide base, and combinations thereof.

Some embodiments provide a multifunctional antimicrobial and analgesic dressing having a backing film and a multifunctional polymer-free clay product. The multifunctional polymer-free clay product includes a clay, a zwitterion, an antimicrobial agent, and, an analgesic. The multifunctional polymer-free clay product provides antimicrobial and pain relieving properties. The backing film is polymeric film impermeable to liquid water.

Some embodiments provide a multifunctional antimicrobial and analgesic dressing having a backing film, a multifunctional polymer-free clay product, and a diffusion control membrane. The multifunctional polymer-free clay product includes a clay, a zwitterion, an antimicrobial agent, and, an analgesic. The multifunctional polymer-free clay product provides antimicrobial and pain relieving properties. The backing film is polymeric film impermeable to liquid water. The diffusion control membrane is a porous layer that provides controlled release of the analgesic in the multifunctional polymer-free clay product.

Some embodiments provide a multifunctional antimicrobial and analgesic dressing having a backing film and more than one multifunctional polymer-free clay product. Each of the multifunctional clay product includes a clay, a zwitterion, an antimicrobial agent, and, an analgesic. The multifunctional antimicrobial and analgesic dressing provides antimicrobial and pain relieving properties. The backing film is a polymeric film impermeable to liquid water.

Some embodiments provide a multifunctional antimicrobial and analgesic dressing having a backing film, more than one multifunctional polymer-free clay product, and a diffusion control membrane. Each of the multifunctional clay product includes a clay, a zwitterion, an antimicrobial agent, and, an analgesic. The multifunctional antimicrobial and analgesic dressing provides antimicrobial and pain relieving properties. The backing film is a polymeric film impermeable to liquid water. The diffusion control membrane is a porous layer that provides controlled release of the analgesic from the multifunctional polymer-free clay product.

BRIEF DESCRIPTION OF THE DRAWINGS

FIGS. 1A and 1B provide photographs. (FIG. 1A) A roll of silver containing claymat loaded with fentanyl demonstrating the flexibility of the mat. (FIG. B) A large sheet of silver containing claymat loaded with fentanyl with 10-inch width and 15-inch length.

FIG. 13A is a simple patch without the drug diffusion controller layer. FIG. 13B includes a drug diffusion controller membrane on top of the analgesic loaded silver containing claymat.

DETAILED DESCRIPTION OF THE INVENTION

Clay Films or Sheets

Figure 2:
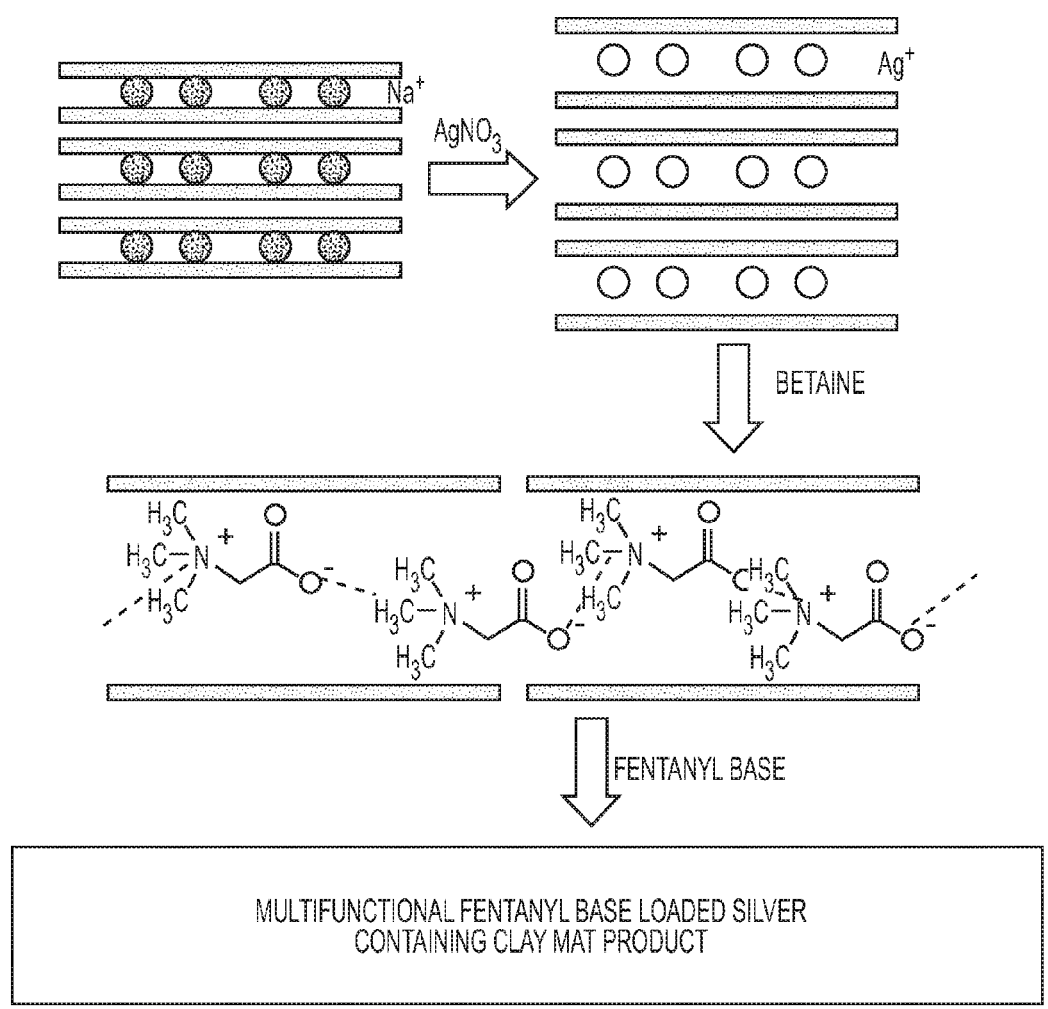
FIG. 2 provides a schematic diagram of ion-exchange of silver ions and intercalation of betaine followed by the addition of analgesic drug fentanyl.

The disclosure relates to preparation, properties, and applications of thin clay sheets.

Montmorillonite clay has excellent adsorbent as well as particle clumping properties. Cations such as sodium, lithium, and potassium reside in the gap between these layers known as the gallery or the interlayer. The gallery allows for 3 processes to occur: hydrophobic modification, intercalation, and exfoliation.

Intercalation is when an organic component is inserted in between the gallery, causing expansion, yet still maintaining a well-defined spatial relationship between the layers. Intercalation causes the gallery to expand up to 1 to 2 angstrom. Exfoliation is a delaminating process where the gallery expands to the point where the layers completely separate from each other. This is accomplished through the adsorption of desired molecules. During exfoliation, packets of clay platelets separate from one another. Platelets at the outermost region of each packet cleave off, exposing more platelets for separation. The gallery expands up to 20 to 30 angstroms in the case of exfoliation, almost 20 times more than intercalation.

The initial question that arose was how to create a clay film that does not fall apart and does not make use of significantly large polymers. Montmorillonite clay naturally forms stacks of plate-like structures called platelets, with each platelet being less than 10 angstroms thick. The gallery spaces between the platelets can be filled with monomers, oligomers, or polymers to increase the distance between the platelets. The clay must expand but not enough to lose its stack organization because if it becomes exfoliated, it will fail to form an intact film.

In some embodiments organo-modified clay sheet made by using zwitterions (ionic compounds containing both positive and negative ions in the same molecule) such as Betaine, Betaine hydrochloride, Choline chloride, [2-(Methacryloyloxy)ethyl]dimethyl-(3-sulfopropyl) ammonium hydroxide, [2-(Methacryloyloxy)ethyl]dimethyl-(3-sulfopropyl) ammonium chloride, 3-Benzyl-5-(2-hydroxymethyl)-4-methylthiazolium chloride and bromide, chloride, fluoride and iodide salts of tetraheptylammonium and cetyltrimethylammonium cations; all of them having a very high charge density to intercalate the clay layer intergallery.

Solvents that can be used for making the clay and organo-modified clay may include water, alcohols, organic solvents such as toluene, dimethyl formamide, dimethyl carbonate, chloroform, and acetonitrile. The drying times required for formation of clay and organo-modified films ranges from about 0 to about 24 days. In some embodiments, the drying time ranges from about 1 minute to about 24 hours. In some embodiments, the drying time ranges from about 5 to about 12 hours. The curing can be accelerated by heating using a microwave, or Ultra Violet radiation or Infrared radiation or conventional heat source. Low humidity can also accelerate the curing.

The disclosed teachings provide preparation of clay in the form of thin film, cut into desirable sizes. The organo-modified clay product is a film, a sheet, a mat, a patch or a membrane. The disclosed organo-modified clay product is referred to as polymer-free because polymer is not added for preparation of the clay product. Others disclose clay products made using polymeric materials, which are commonly known as "polymer-clay composites." In products referred to as polymer-clay composites, the polymers act as a medium to disperse clay particles and to provide mechanical stability to the polymer-clay composite sheets. The polymer-clay composite use various polymeric materials such as polyaniline, polymethyl methacrylate (PMMA), poly (styrene-co-acrylonitrile), polyaniline, polypyrrole, polysulfone, polyacrylates, polyimide, epoxy, polyamide, polypropylene, polypropylene, polyethylene, polystyrene, polyvinylchloride, acrylonitrile butadiene styrene (ABS) polymer, Polyethylene terephthalate (PET), ethylene-vinyl acetate copolymer (EVA), polyacrylonitrile, polycarbonate, polyethylene oxide (PEO), epoxy resin, polyimide, polylactide, polycaprolactone, phenolic resin, poly p-phenylene vinylene, polypyrrole, rubber, starch, polyurethane, and polyvinylpyridine (PVP), cellulose acetate, vinyl acetate resins, acrylic resins, styrene resins, vinyl chloride resins, melamine resins, silicones, polyurethane, polysulphones, polyphenylene ethers, polybutylene terephthalate, and polyethersulfones in their preparation (Fengge Gao, Clay/polymer composites: the story, Materials Today, Volume 7, Issue 11, Pages 50-55, 2004). The disclosed embodiments are referred to as polymer-free because the disclosed products do not require polymers as described above.

The disclosure provides fabrication of a clay film covered with mesh and put onto the adhesive material that serves as the base of the bandage.

Some embodiments use clay film in a wound dressing. Some embodiments use clay film in a burn wound dressing. Some embodiments use clay film in an antimicrobial dressing for gram negative and gram positive bacteria. Some embodiments use clay film in a hemostatic dressing.

Some embodiments use clay film as a permeable and semi-permeable membrane.

The disclosure relates to the synthesis of organo-modified clay films that can be incorporated with metal and non-metallic cations and able to make small to large dimension free standing clay films and membranes upon drying.

Some embodiments prepare clay sheets without using polymers. Because in transdermal drug delivery application, the polymer can hinder or reduce the permeation or diffusion of moisture, chemicals, drugs, analgesics, and local anesthetics through the clay sheets. It is also preferable to have a continuous sheet clay uninterrupted by the polymer matrix. In this way, special properties of clay particles such as adsorption, permeability to drugs and water, high temperature stability, ion-exchange property, chemical permeation property, drug delivery property, chemical diffusion property, hemostasis property, and wound healing property can be fully utilized without being disturbed or hindered by the properties of the polymer.

Some embodiments use clay film as a UV-resistant, IR-resistant, hydrophobic and hydrophilic coating materials.

Organomodified clay can be exchanged with any group I (monocationic), group II (dicationic), group III (tricationic), alkali metal, alkaline earth metal or a combination of groups I, II and III metal species and ions, and nano and micro sized particles form.

Organo-modified clay can be exchanged with any transition metal, late transition metal, lanthanide metal, heavy elements in ionic and nano and micro sized particles form.

Organo-modified clay can be exchanged with organic molecules including but not limited to pharmacological drugs, vitamins, and nutrients Some embodiments use clay sheets to provide controlled delivery of analgesic drugs to burn wounds while assisting in wound healing with its antimicrobial and moisture control properties.

Some embodiments use clay sheets to provide transdermal delivery of nutrients and pharmacological agents.

The disclosure provides a polymer-free organo-modified clay product. The organo-modified clay product has clay and an organic compound. The organo-modified clay product is alternatively referred to in the disclosure as a film, a sheet, a mat, a patch or a membrane. The disclosed organo-modified clay product is referred to as polymer-free because the polymer is not added for preparation of the clay product. The clay is montmorillonite, kaolinite, smectite, and bentonite. The organic compound is betaine, betaine hydrochloride, choline chloride, 3-Benzyl-5-(2-hydroxymethyl)-4-methylthiazolium chloride, 3-Benzyl-5-(2-hydroxymethyl)-4-methylthiazolium bromide, 3-Benzyl-5-(2-hydroxymethyl)-4-methylthiazolium fluoride, [2-(Methacryloyloxy)ethyl]dimethyl-(3-sulfopropyl) ammonium hydroxide, [2-(Methacryloyloxy)ethyl]dimethyl-(3-sulfopropyl) ammonium chloride or 3-Benzyl-5-(2-hydroxymethyl)-4-methylthiazolium iodide.

In some embodiments, a thickness of the polymer-free organo-modified clay product ranges from about 1 micrometer to about 500 micrometers. In some embodiments, a thickness of the polymer-free organo-modified clay product ranges from about 1 micrometer to about 100 micrometers. In some embodiments, a thickness of the polymer-free organo-modified clay product ranges from about 20 micrometers to about 60 micrometers. In some embodiments, a thickness of the polymer-free organo-modified clay product, ranges from about 60 micrometers to about 100 micrometers. In some embodiments, a thickness of the polymer-free organo-modified clay product is about 80 micrometers.

In some embodiments, the polymer-free organo-modified clay product achieves a bending radius of curvature ranging from about 0.4 millimeters to about 10 centimeters. The bending radius of curvature is achieved without breaking the polymer-free organo-modified clay product. In some embodiments, the polymer-free organo-modified clay product achieves a bending radius of curvature ranging from about 0.3 millimeters to about 10 millimeters. In some embodiments, the polymer-free organo-modified clay product achieves a bending radius of curvature of about 0.5 millimeters. In some embodiments, the polymer-free organo-modified clay product achieves a bending radius of curvature of about 0.4 millimeters.

In some embodiments, the polymer-free organo-modified clay product has greater than 50 percent absorption of visible light. In some embodiments, the polymer-free organo-modified clay product is non-transparent. In some embodiments of the polymer-free organo-modified clay product, when the thickness of the product was about 50 micrometers, the film had greater than 50 percent absorption of visible light. In some embodiments, when the organo-modified clay product was further modified by the addition of silver, the film absorbed greater than 82 percent of the visible light.

In some embodiments, the polymer-free organo-modified clay product does not incorporate a polymer. In some embodiments, the organo-modified clay product is a polymer free composite.

Antimicrobial Wound Dressing Application of Clay Sheets

The disclosed organo-modified clay materials stand out from the rest, as till date there is no available literature on synthesis of free-standing organo-modified or unmodified clay films that are prepared without using polymers or binders. Clay tends to swell when water is drawn into the interlayer space, allowing the cations to become easily exchangeable. In some embodiments, an N,N,N-trimethylglycine, also known as Betaine is intercalated into the clay. The hydroxyl groups of clay attach to the Betaine, expanding the clay. The silver ions in silver nitrate exchange with the sodium cations and take their place within the interstitial space as well. The silver ions in silver nitrate, the component added to the Montmorillonite gallery, is the main driving force for eliminating the microbes. Silver ions tend to have antiseptic properties used for controlling burn and eye infections. Silver ions have the ability to disrupt the bacterial cell wall, penetrate the cell and disrupt the physiological function of cell respiration and metabolites. In addition, silver is bactericidal, against more than 150 species of bacteria, viruses, yeast and fungi, including MRSA, MDR, *Klebsiella* and *Pseudomonas* species.

Water acts as an essential component in the antimicrobial bandage as well. Although most of it evaporates after the clay film is cast, some of it may remain within the clay film to provide moisture to the wound.

Organo-modified Silver-clay film can be used as an antimicrobial wound dressing. The bare clay and organo-modified clay films that can be used as burn and or wound bandages with membranes and adhesive patches can also be used to stop bleeding hence can be used as a hemostatic agent or bandage against wound bleeding and healing in 0-100 minutes time interval. The purpose of this product is to fulfill the function of a bandage as well as kill microbes when applied to the wound. The product achieves its purpose of eliminating bacteria in less than 5 min-32 hour depending on the bacterial colony size.

The bandages can be made available in three different film sizes ranging from 0.1 cm by 0.1 cm to 1.00 meter by 100 meter sizes. These sizes are produced to cater to small, medium or large wounds. In some embodiments, the larger film products are also referred to as sheets. In some embodiments, if the size of the wound is small a smaller size of the film product is cut and is referred to as a mat.

The silver clay sheet may also work effectively in eliminating other different types of microbes such as fungi or algae as well.

Silver-clay sheets serve multiple purposes in the burn and scar healing process. Clay has well-known property to retain moisture and has been used as a promoter for hemostasis. Clay with optimal silver concentrations can reduce the cost without compromising the efficacy of the silver.

There is a large amount of clinical evidence to support the use of hydrogel dressings in the treatment of hypertrophic scars. It may be due to the hydrogel dressing's ability to hydrate the damaged tissue and allow oxygen to permeate to the surface of the skin. This will help in a localized increase in oxygen concentration leading to a down-regulation of signals that stimulate growth near the skin surface, thus preventing or reducing scar formation. In some embodiments, the multifunctional polymer-free clay product is oxygen permeable. In some embodiments, the multifunctional polymer-free clay product is oxygen transport rate of at least 100 cubic centimeters per 100 square inches per day.

The final product was easily contoured as a bandage (strip or roll) with a silicone-based hydrogel adhesive. The bandage served as a burn and wound care product, which has a huge commercial market for military and civilian casualties. The wound dressing can be applied to numerous applications, such as burn, wound, and surgical care, and also in water filtration systems and for food packaging.

In some embodiments, the polymer-free organo-modified clay product includes an antimicrobial agent. The antimicrobial agent can be silver ion, copper, iodine, proflavine, silver-containing compounds, copper containing compounds, quaternary ammonium compounds, or quaternary phosphonium compounds. Silver-containing compounds include but are not limited to silver sulfadiazine, silver nitrate, silver oxide, and silver carbonate; copper containing compounds include but not limited to copper oxide, copper sulfate, copper acetate, and copper nitrate; quaternary ammonium compounds include but not limited to benzalkonium alkyl chloride, methyl trialkyl ammonium chloride, and alkyl dimethyl benzyl ammonium chloride and quaternary phosphonium compounds include but not limited to alkyl trimethyl phosphonium chloride and dialkyl dimethyl phosphonium bromide.

In some embodiments, the polymer-free organo-modified clay product includes an analgesic. The analgesic can be opioid analgesics, nonsteroidal anti-inflammatory drugs (NSAIDs) and adjuvant analgesics, capsaicin, clonidine, ketamine, Morphine, fentanyl, Buprenorphine or cannabinoids.

Some embodiments provide an antimicrobial dressing having the polymer-free organo-modified clay product. Some embodiments provide a burn wound dressing having the polymer-free organo-modified clay product.

Some embodiments provide a method of antimicrobial treatment by administering the polymer-free organo-modified clay product.

Some embodiments provide a method of treating burns by administering the polymer-free organo-modified clay product.

Some embodiments provide a method of preparing a polymer-free organo-modified clay product. The method includes mixing a clay particle and an organo-containing solution to form a slurry. Then the slurry is casted on a substrate to obtain a slurry casted on a substrate. Then the slurry casted on the substrate is dried to obtain a dried product of the slurry on the substrate. Then the dried slurry product is separated from the substrate. The separated dried slurry product is the polymer-free organo-modified clay product. The polymer-free organo-modified clay product can be a film, a sheet, a mat or a patch or a membrane. In some embodiments, if the substrate is glass, then the dried slurry product has to be removed from the glass substrate. In some embodiments, if the substrate is fabric or nylon, the dried slurry product need not be removed from the fabric or nylon. The resulting dried slurry product on the fabric or nylon substrate can together form part of a wound dressing product. Thus, dried slurry need not be removed from a nylon or fabric substrate. In this disclosed methods, no polymer has been added to the clay for preparing the product. In some embodiments of the method, the substrate can be a silicone sheet, fabric or a glass surface. In some embodiments, the fabric is nylon.

In some embodiments of the method when the product is prepared at a temperature of about 25 degree C., the viscosity of the slurry prepared for spreading on the substrate ranges from about 2 centipoise to about 20 centipoise. In some embodiments of the method when the product is prepared at a temperature of about 25 degree C., the viscosity of the slurry prepared for spreading on the substrate ranges from about 5 centipoise to about 10 centipoise. In some embodiments drying the slurry casted on the substrate is performed under conditions of slow, air. In some embodiments drying the slurry casted on the substrate is performed at 20-25 degrees Centigrade under ambient, room temperature conditions.

In some embodiments, the polymer-free organo-modified clay product has greater than 16 grams per square meter per hour water vapor transport rate (WVTR) at 40 degree C.

Some embodiments provide a method of preparing a polymer-free organo-modified clay product. The method includes mixing a clay particle and an organo-containing solution to form a slurry. Then the slurry is casted on a substrate to form a slurry casted on a substrate product. Then the slurry casted on the substrate is dried to obtain the polymer-free organo-modified clay product. The organo-modified clay product can be a film, a sheet, a mat or a patch or a membrane.

Some embodiments provide a method of preparing a polymer-free organo-modified clay product having an antimicrobial agent. The method includes mixing a clay particle and an organo-containing solution. Then an antimicrobial agent containing solution is added to obtain a slurry. The slurry is casted onto a substrate. The casted slurry and substrate are subjected to drying, and a dried slurry is obtained on the substrate. The dried slurry is separated from the substrate to obtain the organo-modified clay product containing the antimicrobial agent.

Some embodiments pro vide a method of preparing a polymer-free organo-modified clay product having an analgesic. The method includes mixing a clay particle and an organo-containing solution. Then an analgesic containing solution is added, and a slurry is obtained. The slurry is casted on a substrate and dried to obtain a dried slurry on the substrate. The dried slurry is separated from the substrate to obtain the polymer-free organo-modified clay product having the analgesic compound.

Some embodiments provide an antimicrobial wound dressing that also has analgesic properties. The wound dressing has a polymer-free organo-modified clay product having an antimicrobial agent. The wound dressing has successive layers of the following: a hydrogel adhesive with a hydrophobic backing; a polymer-free organo-modified clay product having an antimicrobial agent and analgesic; and, a nylon membrane.

Some embodiments provide a method of preparing an antimicrobial wound dressing having analgesic properties. The method includes successively layering the following: a hydrogel adhesive with a hydrophobic backing; a polymer-free organo-modified clay product having an antimicrobial agent; and, a nylon membrane. In some embodiments, the method includes successively layering the following: a nylon membrane, then a polymer-free organo-modified clay product having an antimicrobial agent and analgesic; and, then a hydrogel adhesive with a hydrophobic backing.

Some embodiments provide an analgesic wound dressing. The analgesic wound dressing includes a polymer-free organo-modified clay product having an analgesic. The wound dressing has successive layers of the following: a hydrogel adhesive with a hydrophobic backing; a polymer-free organo-modified clay product having an analgesic and, a nylon membrane. Some embodiments provide a transdermal wound dressing. Some embodiments provide a method of preparing a transdermal wound dressing.

Some embodiments provide a method of preparing an analgesic wound dressing. The method includes successively layering the following: a hydrogel adhesive with a hydrophobic backing; then a polymer-free organo-modified clay product having an analgesic and, then a nylon membrane. Alternatively, the successive layering can be as follows: nylon membrane, then a polymer-free organo-modified clay product having an analgesic followed by a hydrogel adhesive with a hydrophobic backing.

The disclosure relates to a multifunctional device which could be a patch or bandage or dressing capable providing pain release while acting as antimicrobial.

Silver ions from silver nitrate, exchange with the sodium cations present in clay, within the interstitial space. The silver exchanged clay gallery is the main driving force for eliminating the microbes or bacteria. The organo-modified Silver-Betaine-Clay film is conformable to various shapes and sizes and garners anti-microbial properties. FIG. 1A shows a photograph of silver containing clay mat demonstrating the flexibility of the mat. Large size samples, for example, having 10 inches width and 15 inches length of silver containing claymat such as in FIG. 1B can be made by the disclosed processes. Continuous rolls of mats also can be made by increasing the drying rate using higher temperature and air flow over the mats.

Some embodiments are a clay mat loaded with silver and fentanyl. Some embodiments provide a clay mat loaded with silver and Lidocaine base. Some embodiments provide a clay mat loaded with silver and loperamide base. Some embodiments provide a multifunctional product containing more than one type of clay mat loaded with silver and analgesics. Some embodiments provide a multifunctional product containing both clay mat loaded with silver and fentanyl and clay mat loaded with silver and Lidocaine base. Some embodiments provide a multifunctional product containing both clay mat loaded with silver and fentanyl and clay mat loaded with silver and Loperamide base.

The disclosed teachings provide making of a pain relieving device based on clay mat. The disclosure provides a device based on clay mats with combined antimicrobial and pain relieving properties. The disclosure provides clay mat loaded with silver and analgesics.

The disclosed teachings provide making of a pain relieving device based on clay mat. The disclosure provides a device based on clay mats with combined antimicrobial and pain relieving properties. The disclosure provides clay mat loaded with silver and analgesics. The disclosure provides clay mat loaded with silver and fentanyl.

Some embodiments provide a multifunctional topical wound dressing capable of both antimicrobial action while delivering pain medication.

Some embodiments provide a multifunctional polymer-free clay product having a clay, a zwitterion, an antimicrobial agent, and, an analgesic. The multifunctional polymer-free clay product provides antimicrobial and pain relieving properties. The clay can be montmorillonite, kaolinite, smectite, and bentonite. The antimicrobial agent can be silver ion, copper, silver-containing compounds, and, copper containing compounds. Silver-containing compounds include but not limited to silver sulfadiazine, silver nitrate, silver oxide, and silver carbonate. The silver provides antimicrobial properties. The zwitterion can be betaine, betaine hydrochloride, choline chloride, 3-Benzyl-5-(2-hydroxymethyl)-4-methylthiazolium chloride, 3-Benzyl-5-(2-hydroxymethyl)-4-methylthiazolium bromide, 3-Benzyl-5-(2-hydroxymethyl)-4-methylthiazolium fluoride, [2-(Methacryloyloxy)ethyl]dimethyl-(3-sulfopropyl) ammonium hydroxide, [2-(Methacryloyloxy)ethyl]dimethyl-(3-sulfopropyl) ammonium chloride and 3-Benzyl-5-(2-hydroxymethyl)-4-methylthiazolium iodide. The analgesic can be opioid analgesics, nonsteroidal anti-inflammatory drugs (NSAIDs) and adjuvant analgesics, capsaicin, clonidine, ketamine, Morphine, fentanyl, Buprenorphine, fentanyl base, lidocaine base, loperamide base, cannabinoids, and combinations thereof. The thickness of the multifunctional polymer-free clay product ranges from about 1 micrometer to about 500 micrometers. In some embodiments, the thickness of the multifunctional polymer-free clay product ranges from about 1 micrometer to about 100 micrometers. The polymer-free clay product achieves a bending radius of curvature ranging from about 0.4 millimeters to about 10 centimeters. The polymer-free clay product can have greater than 50 percent absorption of visible light. The polymer-free clay product does not incorporate a polymer. Some embodiments provide a multifunctional dressing having a multifunctional polymer-free clay product.

Some embodiments provide a method of treating burns by administering a multifunctional polymer-free clay product having antimicrobial and pain relieving properties.

Some embodiments provide a method of preparing a multifunctional polymer-free clay product having an antimicrobial and an analgesic. The method includes mixing a clay, an antimicrobial agent, and water to form a first clay slurry. Washing the first clay slurry with water to obtain a washed second clay slurry. Next, adding a zwitterion and water to the washed second slurry to obtain a third clay slurry. Then casting the third clay slurry onto a substrate to obtain a first dried product. Then adding drops of analgesic in a non-aqueous solvent onto the first dried product to obtain a resultant product. Then drying the resultant product to obtain a second dried product. Then separating the second dried from the substrate. The second dried product is the multifunctional polymer-free clay product. The multifunctional polymer-free clay product provides both antimicrobial and pain relieving properties. The antimicrobial in the multifunctional polymer-free clay product can be silver ion, copper, silver-containing compounds, and, copper containing compounds. In some embodiments, the silver compound is silver nitrate. The analgesic can be fentanyl, lidocaine base, loperamide base, and combinations thereof. The substrate can be a silicone sheet, fabric, and a glass surface. The clay can be montmorillonite, kaolinite, smectite, and bentonite. The zwitterion can be betaine, betaine hydrochloride, choline chloride, 3-Benzyl-5-(2-hydroxymethyl)-4-methyl-thiazolium chloride, 3-Benzyl-5-(2-hydroxymethyl)-4-methylthiazolium bromide, 3-Benzyl-5-(2-hydroxymethyl)-4-methylthiazolium fluoride, [2-(Methacryloyloxy)ethyl]dimethyl-(3-sulfopropyl) ammonium hydroxide, [2-(Methacryloyloxy)ethyl]dimethyl-(3-sulfopropyl) ammonium chloride and 3-Benzyl-5-(2-hydroxymethyl)-4-methylthiazolium iodide.

In another embodiment of the method of preparing a multifunctional polymer-free clay product having an antimicrobial and an analgesic, the method includes mixing a clay, an antimicrobial agent, and water to form a first clay slurry. Then washing the first slurry with water to obtain a washed second clay slurry. Then adding a mixture of water and a non-aqueous solvent containing betaine and an analgesic to the washed second slurry to obtain a third clay slurry. Next, casting the third clay slurry onto a substrate to obtain a dried product. Next, separating the dried product from the substrate to obtain a separated dried product. The separated dried product is the multifunctional polymer-free clay product, which provides antimicrobial and pain relieving properties. The antimicrobial agent can be silver ion, copper, silver-containing compounds, and, copper containing compounds. In some embodiments, the silver compound is silver nitrate. The analgesic can be fentanyl, lidocaine base, loperamide base, and combinations thereof. Fentanyl compounds include but not limited to fentanyl base, fentanyl citrate, and fentanyl hydrochloride (R. S. Vardanyan, V. J. Hruby, Fentanyl-related compounds, and derivatives: current status and future prospects for pharmaceutical applications. Future medicinal chemistry, 6(4), 385-412, 2014).

Figure 13A:
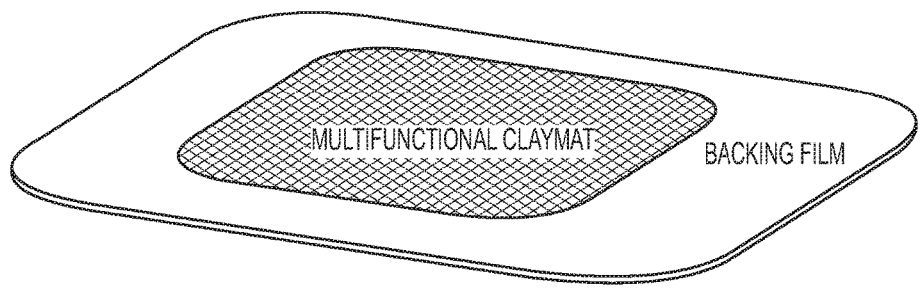
FIGS. 13A and 13B provide a schematic diagram of analgesic loaded silver containing claymat patches.

Some embodiments provide a method of preparing a multifunctional wound dressing as shown FIG. 13A. The method includes successively layering of the following: a hydrophobic backing film; a multifunctional polymer-free organo-modified clay product having both an antimicrobial agent and an analgesic.

Backing Layer

In some embodiments, a backing layer may be present. The backing layer is typically a layer farthest from the wound. The backing layer provides support to the multifunctional claymat and can increase the mechanical strength of the wound dressing. Preferably the backing layer is conformable to animal anatomical surfaces and impermeable to liquid water.

The backing layer can be an occlusive dressing that is impermeable to analgesics, and anesthetics and other drugs. The backing layer can be a plastic sheet laminated with metallic foil.

The backing layer can be a transparent, opaque, conformable, elastomeric, moisture vapor permeable film. The backing film is preferably impermeable to liquid water. The backing films may be permeable to water vapor. The dressing is preferably conformable to anatomical surfaces and stretches to the movement of skin and contracts back to the same size as before stretching. The backing layer may further include a pressure sensitive adhesive layer to enhance adhesion to the first absorbent layer. The backing film may be made up using a hydrogel. The backing film may be hydrophobic and repel water.

In some embodiment of the invention, the backing layer can be a dressing such as that sold under the trademark Tegaderm (3M, St. Paul Minn.). The backing layer can be used to cover and protect dressing and wounds, to maintain a moist environment for wound healing, as a protective cover over the wound site.

Backing layer could be non-woven fabrics, natural fiber (e.g., cotton) fabrics, synthetic resin fabrics, synthetic resin films, gauze dressing, synthetic resin foams, woven, fabrics, and knit fabrics. Pressure-sensitive adhesive sheets, pressure-sensitive adhesive dressings, hydrogel dressings, can also be used as a backing layer.

Some embodiments provide a multifunctional antimicrobial and analgesic dressing having a backing film and a multifunctional polymer-free clay product. The multifunctional polymer-free clay product includes a clay, a zwitterion, an antimicrobial agent, and, an analgesic. The multifunctional polymer-free clay product provides antimicrobial and pain relieving properties. The backing film is polymeric film impermeable to liquid water.

Some embodiments provide a multifunctional wound dressing consists of successively layering of the following: a hydrophobic backing film; a polymer-free organo-modified day product having both silver and fentanyl.

Some embodiments provide a multifunctional wound dressing consists of successively layering of the following: a hydrophobic backing film; a polymer-free organo-modified clay product having both silver and lidocaine base.

Diffusion Control Membrane

The multifunctional dressing can include a porous diffusion control layer to provide a controlled release of analgesic from multifunctional clay mat to the wound site.

The diffusion barrier membrane allows transport of analgesic from the multifunctional clay mat to wound site. The diffusion barrier membrane also allows moisture, perspiration and wound exudates from the wound to the multifunctional claymat. This diffusion layer allows isolation of wound site from other components of the dressing. The diffusion control membrane is preferably soft, flexible, and conformable. It should also be non-irritating to skin or wound. Typically, polymeric membranes are used to control the rate of drug release in transdermal patches. Polymeric membranes can be made of a polymer such as but not limited to nylon, polyurethane, Polytetrafluoroethylene, polyethylene, polypropylene, polyamide or polyester materials. Further, the diffusion control membrane may be in the form of moisture vapor permeable films, perforated films, porous films, films with micron-sized holes, films with nano-sized holes, track-etched polymer membranes, woven-, non-woven or knit webs, or scrims. Some embodiments of the diffusion membrane are a nylon membrane. In some embodiments, the diffusion control membrane can be a thin perforated polymeric film such as that sold under the trademark Delnet manufactured by Applied Extrusion Technologies, Inc., of Middletown Del.

Figure 13B:
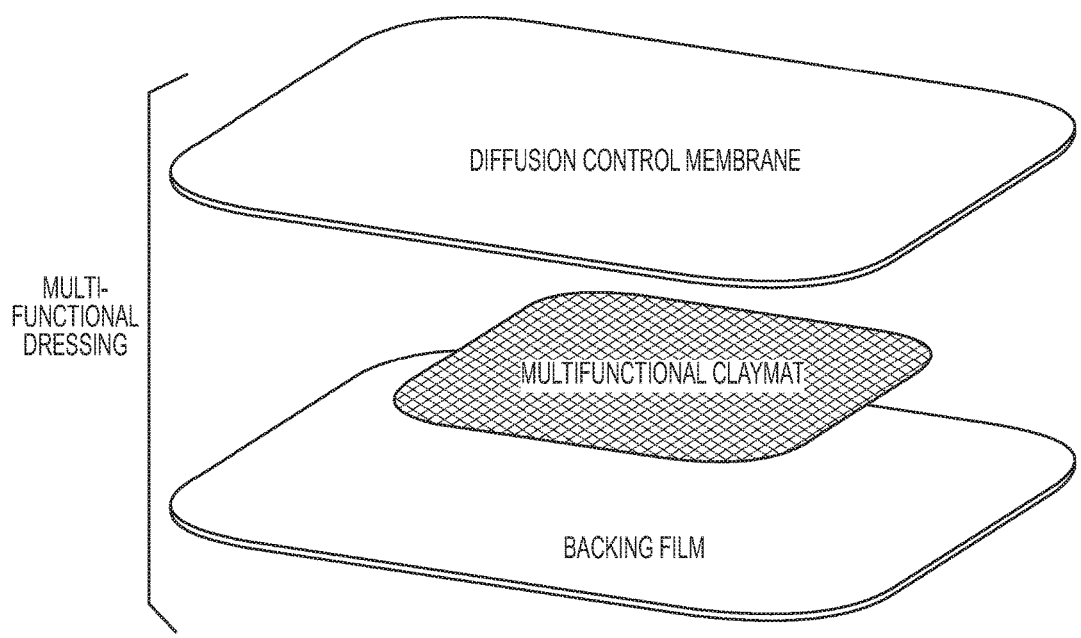

Some embodiments provide a method of preparing a multifunctional wound dressing as shown in FIG. 13B. The method includes successively layering of the following: a hydrophobic backing film; a multifunctional polymer-free organo-modified clay product having both an antimicrobial agent and an analgesic and, a diffusion control membrane.

Some embodiments provide a multifunctional antimicrobial and analgesic dressing having a backing film, a multifunctional polymer-free clay product and a diffusion control membrane. The multifunctional polymer-free clay product includes a clay, a zwitterion, an antimicrobial agent, and, an analgesic. The multifunctional polymer-free clay product provides antimicrobial and pain relieving properties. The backing film is polymeric film impermeable to liquid water. The diffusion control membrane is a porous layer that provides controlled release of the analgesic in the multifunctional polymer-free clay product.

Some embodiments provide a multifunctional wound dressing. The multifunctional wound dressing includes a polymer-free organo-modified clay product having both an antimicrobial agent and an analgesic. The wound dressing has successive layers of the following: a hydrogel adhesive with a hydrophobic backing; a polymer-free organo-modified clay product having both an antimicrobial and an analgesic and, a nylon membrane. Some embodiments provide a transdermal wound dressing. Some embodiments provide a method of preparing a transdermal wound dressing.

Some embodiments provide a multifunctional wound dressing. The multifunctional wound dressing includes a polymer-free organo-modified clay product having both silver and fentanyl. The wound dressing has successive layers of the following: a hydrogel adhesive with a hydrophobic backing; a polymer-free organo-modified clay product having both having both silver and fentanyl and, a nylon membrane. Some embodiments provide a transdermal wound dressing. Some embodiments provide a method of preparing a transdermal wound dressing.

Some embodiments provide a multifunctional wound dressing. The multifunctional wound dressing includes a polymer-free organo-modified clay product having both silver and lidocaine base. The wound dressing has successive layers of the following: a hydrogel adhesive with a hydrophobic backing; a polymer-free organo-modified clay product having both having both silver and lidocaine base and, a nylon membrane. Some embodiments provide a transdermal wound dressing. Some embodiments provide a method of preparing a transdermal wound dressing.

Figure 14:
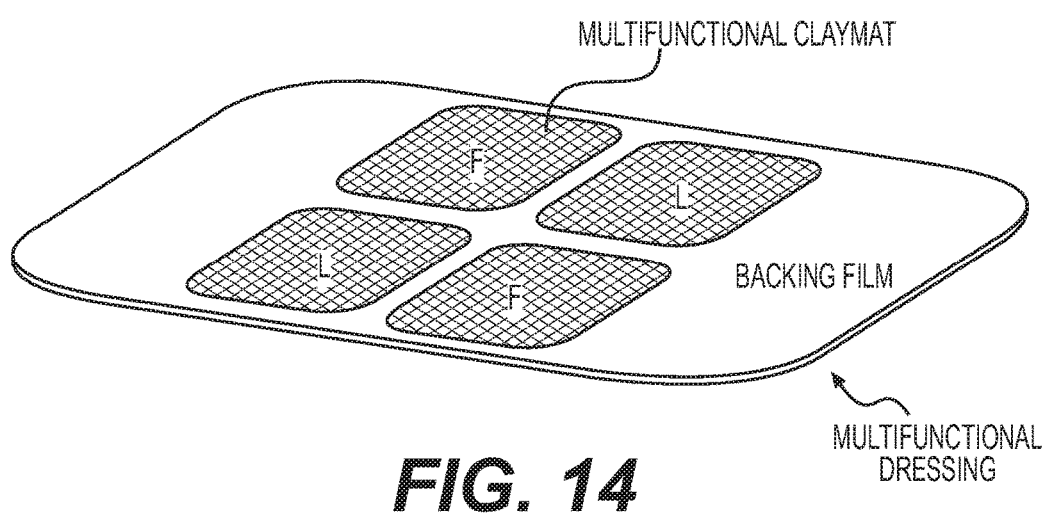
FIG. 14 provides the schematic diagram of a multifunctional dressing consisting of more than one silver containing claymat. Each silver containing claymat is loaded with a different drug (for example, F=Fentanyl loaded silver containing claymat, L=Lidocaine base loaded silver containing claymat).

Some embodiments provide a method of making clay mat with analgesics. Some embodiments are a method of making clay mat with fentanyl. Some embodiments are a method of making clay mat with Lidocaine base. Some embodiments are a method of making clay mat with Loperamide base. Some embodiments provide a multifunctional wound dressing. The multifunctional wound dressing includes a polymer-free silver containing clay product having a pain relieving drug. Some embodiments provide a multifunctional wound dressing containing more than one type of polymer-free silver containing clay product having a pain relieving drug, where the pain relieving drug could be an analgesic such as fentanyl, morphine but not limited to and a local anesthetic such as lidocaine base or loperamide base but limited to. One embodiment is represented in FIG. 14. FIG. 14 shows a multifunctional dressing that has more than one multifunctional polymer-free clay product. Some of the multifunctional polymer-free clay products have fentanyl (shown as F). Some of the multifunctional polymer-free clay products have lidocaine (indicated as L).

Some embodiments provide a multifunctional antimicrobial and analgesic dressing having a backing film and more than one multifunctional polymer-free clay product. Each of the multifunctional clay product includes a clay, a zwitterion, an antimicrobial agent, and, an analgesic. The multifunctional antimicrobial and analgesic dressing provides antimicrobial and pain relieving properties. The backing film is a polymeric film impermeable to liquid water.

Some embodiments provide a multifunctional antimicrobial and analgesic dressing having a backing film, more than one multifunctional polymer-free clay product, and a diffusion control membrane. Each of the multifunctional, clay product includes a clay, a zwitterion, an antimicrobial agent, and, an analgesic. The multifunctional antimicrobial and analgesic dressing provides antimicrobial and pain relieving properties. The backing film is a polymeric film impermeable to liquid water. The diffusion control membrane is a porous layer that provides controlled release of the analgesic from the multifunctional polymer-free clay product.

In some embodiments, a multifunctional antimicrobial and analgesic dressing having a backing film is provided that has more than one polymer-free clay product. One of the polymer-free clay products includes a clay, a zwitterion, and an antimicrobial agent. Another of the polymer-free clay products includes a clay, a zwitterion, and an analgesic. Preparation of such separate polymer-free clay products that individually include antimicrobial or analgesic is disclosed in parent applications. The combination of polymer-free clay products providing antimicrobial or analgesic properties results in a multifunctional antimicrobial and analgesic dressing that provides both antimicrobial and pain relieving properties. The backing film for the multifunctional dressing is a polymeric film impermeable to liquid water. Additionally, the dressing can include a diffusion control membrane to provide controlled release properties.

Some embodiments provide multifunctional topical wound dressing capable of both antimicrobial action while delivering pain medication.

Processes in which analgesic such as but not limited to fentanyl, and morphine and local anesthetics such as but not limited to lidocaine base and loperamide base is incorporated into the clay mat is provided.

In one embodiment, the silver containing claymats can be dipped in analgesic or local anesthetic drug dissolved in a non-aqueous solution for a period of time. In this process, the drug was absorbed by the silver containing claymat.

In another embodiment, drops of a non-aqueous solution of analgesic or local anesthetic drug were placed on the silver containing claymat to allowed to be absorbed into the claymat. Then the solvent was evaporated to produce drug-loaded silver containing claymat.

In another embodiment, silver ion-exchanged clay particles were treated with a mixture of water and a non-aqueous solvent containing both betaine and analgesic or local anesthetic drugs. Then the resulting slurry will be casted onto a substrate and allowed to dry. The resulting dried product is the silver containing drug loaded clay mat.

One embodiment of preparation of silver containing claymats is as follows. Montmorillonite clay slurry was formed by ion-exchanging sodium ions in the clay with silver ions, followed by intercalating with anhydrous trimethylglycine (Betaine) molecules into the interlayer galleries of clay particles. Further drugs such as fentanyl base can be loaded onto the mat to obtain the multifunctional fentanyl base containing clay mat product.

Schematic representation method of the preparation of silver containing claymat is provided in FIG. 2.

It was determined that the sequence of stops involved in the mixing of clay with betaine and silver ions is critical for loading analgesics such as fentanyl.

The order could be the montmorillonite clay ion-exchanges with silver ions first followed by interaction with betaine, or the montmorillonite clay particles were first exfoliated with betaine molecules and then the slurry was treated with silver nitrate.

There is a distinct difference that can be observed on the Silver containing mats obtained from these two sequential routes. The first process yielded a brown sheet probably due to the formation of nano-silver particles inside the galleries of clay layers. In the second process, bulk silver (or micro-sized silver particles) was deposited on the Silver containing claymat resulting in a gray colored product. The Higher amount of Fentanyl was incorporated into the samples, which were formed by first silver ion exchange followed by Betaine loading. If this order is reversed no drug was incorporated into the silver containing claymat.

Another embodiment of a process for incorporating an analgesic drug into silver containing claymat is as follows.

According to one process, the equilibration of silver containing clay patches in fentanyl solution yielded patches with a maximum fentanyl loading of micrograms per sq·cm. The fentanyl loading process was modified in order to increase the loading level of analgesic. In a modified process silver containing claymat patches were first wetted with fentanyl solution in methanol. The fentanyl liquid was absorbed immediately into the claymat due to its porous nature. The solvent was evaporated under ambient conditions leaving fentanyl loaded into the silver containing claymats (Fentanyl is non-volatile with melting point of ~87.5 degree C.). Using this modified method, fentanyl loading levels as high as ~80 micrograms per sq·cm have been achieved.

A process for loading large quantities of the analgesic drug into a silver containing claymat is as follows. The transdermal absorption of opioid analgesics such as fentanyl may take up to 8-12 h to take pain relieving action. However, the injured patient requires the drugs to provide immediate relief. One approach is to use local anesthetics such as Lidocaine or loperamide instead of or in combination with opioid analgesics like Fentanyl.

The lidocaine patch 5 percent (for example, Lidoderm, Endo Pharmaceuticals, Inc., Chadds Ford, Pa.) is a targeted peripheral analgesic, designed to treat peripheral neuropathic pain with minimal risk of systemic adverse effects. The patch facilitates lidocaine diffusion across the skin, where the drug binds to sodium channels that are present in abnormally high numbers on hyperactive or damaged nociceptors. When bound to these sodium channels, lidocaine reduces the abnormal ectopic discharges produced by damaged and dysfunctional peripheral nerves and interrupts conduction of the pain signal, thus alleviating pain. This system presents lidocaine from entering the plasma in any clinically meaningful concentrations.

The commercially available lidocaine patch typically consists of a 10×14 cm, nonwoven, polyethylene backing and medication-containing adhesive of 5 percent lidocaine (700 mg patch) and other inactive ingredients. The lidocaine base amount in these patches is relatively much higher than Fentanyl patches. This could be due to the milder analgesic action of Lidocaine compared to Fentanyl. Therefore, it was decided to prepare silver containing claymat patches with lidocaine with higher loading.

Figure 3:
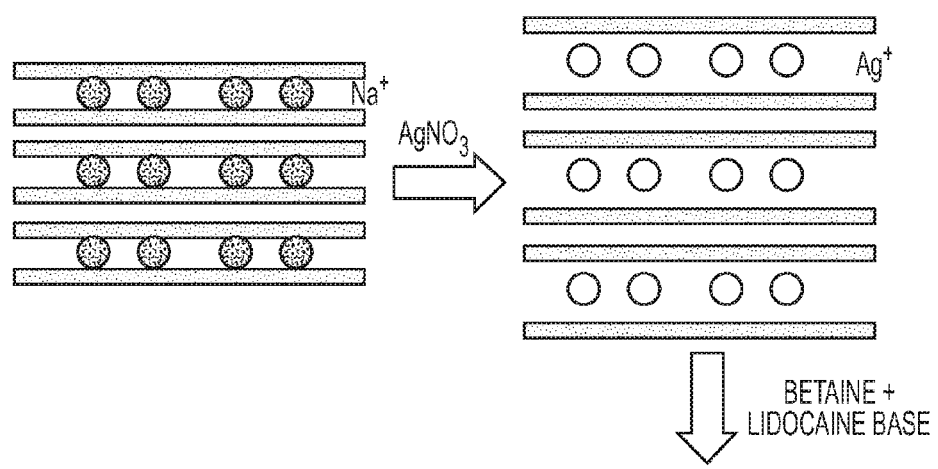
FIG. 3 provides a schematic diagram of ion-exchange of silver ions and the addition of a mixture containing both betaine and a local anesthetic lidocaine base.

Fentanyl solution was dropped onto Silver containing claymat directly, and the solvent was evaporated to form a dry Fentanyl-loaded Silver containing claymat. This method allowed loading of up to 80 microgram/cm$^2$ of fentanyl onto Silver containing claymat. This method is not suitable to load 5000 microgram/sq·cm (5 milligrams per sq·cm or 5 percent) of Lidocaine base typically used in commercial lidocaine patch. Therefore, an alternate method was investigated to load higher amount of lidocaine onto silver containing claymat. According to the new method, the drug was added during the preparation claymats along with betaine as shown in FIG. 3. FIG. 3 shows ion-exchange of silver ions and intercalation of betaine mixed together with lidocaine base to obtain a multifunctional lidocaine base loaded silver containing clay mat product.

Mixtures of silver nitrate and montmorillonite Clay dressing were prepared with different lidocaine hydrochloride compositions. Increasing the lidocaine hydrochloride content in the formulation decreased the stability of claymat formation. Higher level loading of lidocaine hydrochloride (greater than 7.5 weight percent) resulted in flocculation or precipitation of the clay, resulting in claymats that were cracked and poor in quality. Flocculation can be reduced by ion-exchanging silver ions for sodium ions in the clay. However, all these mats were very fragile, broken easily and had poor bending strength. The flexibility of the films can be improved by increasing the betaine content in the film from 15 weight percent to 25 weight percent at the lidocaine hydrochloride loading of 7.5 weight percent.

Since silver-exchanged clays provided better claymats after lidocaine hydrochloride loading, further optimization was carried out using these compositions. The skin penetration of Lidocaine hydrochloride continued to increase with time up to 2.5 hours. However, the amount of drug released was very low, 4 microgram per sq·cm after 2.5 hours. Lidocaine hydrochloride molecules were strongly bound to the claymat through an intercalation process. This strong binding probably is the reason for non-leaching of lidocaine hydrochloride from the silver containing claymat samples. Therefore, a neutral lidocaine base was used instead of lidocaine hydrochloride to increase the release of lidocaine from the claymats and silver containing claymats.

In Vivo Animal Studies:

A prototype topical dressing was tested with an animal (rat) pain model (Hot plate test). Pain response in animals can be measured with the hot plate test. This test can also be used to test the efficacy of analgesics by observing the reaction to pain caused by heat. The main behavioral reaction to heat-induced pain in rats in this system is licking of the hind paws (in response to moderate heat, 48.5 degree C.). The delay in time before a rat exhibits this behavior after exposure to heat is labeled as the paw withdrawal latency (PWL). A higher PWL value indicates less pain (or increased delay of pain) felt by the animal. The test equipment consists of a thermo-regulated hot plate upon which a glass enclosure was placed to keep the rat over the heated surface. The rat was placed on the hot plate and the percentage of time the animal stayed on the hot plate was measured. The animal was able to stay for a longer duration due to the local anesthetic action of fentanyl.

About 112 percent increase in the PWL for rats treated with fentanyl loaded silver containing claymat was observed compared to an untreated animal. It should also be noted that the blank silver containing claymat patch without the fentanyl exhibited about a 25 percent decrease in PWL values. Without wishing to bound by any theory, the reason for this behavior could be the result of silver in the patch, coating the hind paw surface and making the skin more conductive to heat. Interestingly, a longer latency was observed with fentanyl loaded silver containing claymat patch despite the fact that silver increases thermal conductivity, making the argument even stronger that local delivery of fentanyl works as an analgesic.

In summary, the feasibility of silver loaded claymat to act as a topical dressing for the delivery of opioid analgesic, fentanyl has been clearly demonstrated. Both in-vitro (permeation testing with Franz cell) as well as hot plate rat model testing showed that fentanyl can be loaded onto silver containing claymat and can be released in a controlled manner via the skin. Most notable observation is that fentanyl topical patch can be used for local pain relief.

Evaluation of Antinociceptive Activity of lidocaine base loaded silver containing claymat patches:

Plain patches of size 10×10 mm were cut and weighed. 20 microliter of 250 mg per mL (5 mg per sq·cm) of lidocaine base solution in methanol was loaded carefully by adding dropwise using micropipette for each patch. Methanol was allowed to evaporate at room temperature. In one batch of patches, Fentanyl was also loaded similarly. Paw Withdrawal Latency (PWL) of the silver containing claymat loaded with Lidocaine base group was reduced by about 52 percent. On the other side, in the case of plain clay patch (without silver), there was no significant increase in the PWL. However, in the case of plain clay patch (without silver) loaded with lidocaine base PWL increased by about 62 percent. The PWL increased about 103 percent as anticipated in the silver containing claymat patch loaded with Lidocaine base (5 milligrams per sq·cm) and Fentanyl (1 milligram per sq·cm) which was comparable to the positive control commercial Lidoderm patch which resulted in an increase of about 96 percent in the PWL.

Antimicrobial Testing of Fentanyl loaded silver containing claymat samples:

Kirby-Bauer agar diffusion assay for the following samples was conducted using four strains *E. coli, Salmonella Typhimurium, Staphylococcus aureus*, and *Streptococcus pyogenes*. (a) Positive control (Amoxicillin/clavulanic acid—30 ug—BBL sensidisc Product number 231628), (b) Pristine montmorillonite claymat, (c) silver containing clay and (d) Fentanyl-loaded Silver containing claymat.

The positive control, silver containing clay and fentanyl-loaded silver containing claymat samples exhibited a zone of inhibition for all 4 bacteria tested. Further, no significant difference was observed between silver containing clay and fentanyl-loaded silver containing claymat samples. This has clearly demonstrated that antimicrobial action of Silver ion was not detrimentally affected by the fentanyl-loading. The pristine clay material did not show any zone of inhibition, indicating that the montmorillonite clay was not antimicrobial. However, it is important to note here that montmorillonite clay can be replaced with clays that have an inherent antimicrobial property, such as Cloisite 20A and Cloisite 30B [S. I. Hong and J. W. Rhim, Antimicrobial activity of organically modified nano-clays. J. Nanosci Nanotechnol. 8, 5818-24 (2008).].

It will be readily understood by the skilled artisan that numerous alterations may be made to the examples and instructions given herein. These and other objects and features of present invention will be made apparent from the following examples. The following examples as described are not intended to be construed as limiting the scope of the present invention.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

EXAMPLES

Example 1

15 g of montmorillonite clay, 1.53 g silver nitrate, and 250 mL distilled water were mixed in a plastic bottle and then placed in a ball mill. After the mixture had been agitated for at least 18 hours on the ball mill, it was then centrifuged and washed four times with distilled water. The mixture was then put back into the plastic bottle with 2.6 g of Betaine (Sigma-Aldrich, Saint Louis, Mo., CAS number 107-43-7, product number 61962), and enough distilled water added to equal a total of 300 grams of solution and then placed in a ball mill for at least another 18 hours. The mixture was casted onto a silicone mat and allowed to dry. The dried silver containing claymat was used for loading analgesic drugs.

Example 2

Loading of Fentanyl Base onto Silver Containing Claymats

The claymats were cut into definite size. They were weighed and immersed in 1 mg/ml Fentanyl base solution (5 ml) (Sigma-Aldrich, Saint Louis, Mo., CAS number 437-38-7, product number F-013) in a well-sealed container and allowed to equilibrate for 24 hours. The patches were washed off using methanol to get rid of the surface drug completely. The patches were then dissolved in water, centrifuged and the supernatant was collected. The supernatant was filtered through 0.22-micron filter, and then the amount of fentanyl base in the sample was quantitated.

TABLE 1

The amount of drug loaded in thinner Silver containing claymat patches

| Product code | Fentanyl base per unit area (mcg/mg) | Fentanyl base per unit weight (mcg/cm$^2$) |
| --- | --- | --- |
| MMI-1413 | 0.33 ± 0.18 | 1.99 ± 0.73 |
| MMI-1414 | 0.54 ± 0.16 | 3.45 ± 0.91 |
| MMI-1415 | 0.02 | 0.008 |
| MMI-1416 | 0.03 | 0.005 |

The Higher amount of Fentanyl base was incorporated into the samples MMI-1413 and MMI-1414, which were formed by first silver ion exchange followed by Betaine loading. If this order is reversed, no drug was incorporated into the claymat.

The equilibration of Silver containing claymat patches in fentanyl base solution yielded patches with a maximum fentanyl loading of ~8 micrograms per sq·cm. The fentanyl base loading process was modified in order to increase the loading level of fentanyl base. In the modified process Fentanyl base loaded sliver containing claymat patches were first wetted with fentanyl base solution in methanol. The fentanyl base liquid was absorbed immediately into the silver containing claymat due to its porous nature. The solvent was evaporated under ambient conditions leaving fentanyl base loaded into the silver containing claymats (Fentanyl base is non-volatile with melting point of ~87.5 degree C.). Using this modified method, fentanyl loading levels as high as ~80 mcg/cm$^2$ have been achieved.

TABLE 2

The amount of Fentanyl base loaded in silver containing claymat patches (mcg = microgram)

| Product code | Thickness (micrometer) | Fentanyl base loading method | Fentanyl per unit weight (mcg/cm$^2$) |
|---|---|---|---|
| MMI-1413 | 40 | Equilibrating patch with Fentanyl base solution | 1.99 ± 0.73 |
| MMI-1414 | 40 | Equilibrating patch with Fentanyl base solution | 3.45 ± 0.91 |
| MMI-1440 | 80 | Equilibrating patch with Fentanyl base solution | 8.35 ± 2.18 |
| MMI-1441 | 100 | Addition of Fentanyl base solution onto the claymat, followed by solvent removal | 84.54 ± 11.14 |

Examples 3

In-Vitro Drug Release Studies

Initial trials were performed using Franz diffusion cells. The films (MMI-413 and MMI-1414) dissolved in water and buffer. Therefore, we performed the release studies using methanol. The films were immersed in 4 ml methanol. 200 microliters of methanol were sampled at each time point, and the reservoir was replaced with same volume each time. The amount of drug in methanol was quantitated by HPLC. The amounts of fentanyl released into the solution were provided in Table 3 and 4.

TABLE 3

Drug release per unit area of the Fentanyl loaded silver containing claymat mat

| Time (h) | MMI-1413 (mcg/cm$^2$) | MMI-1414 (mcg/cm$^2$) | sd | sd |
|---|---|---|---|---|
| 0 | 0.09 | 0.42 | 0.017 | 0.09 |
| 1.5 | 0.84 | 1.45 | 0.02 | 0.02 |
| 3 | 1.64 | 2.40 | 0.84 | 0.11 |
| 5 | 1.86 | 3.34 | 0.93 | 0.62 |
| 7 | 1.98 | 3.46 | 0.72 | 0.63 |

TABLE 4

Drug release per unit weight of the Fentanyl loaded silver containing claymat mat

| Time (h) | MMI-1413 (mcg/cm$^2$) | MMI-1414 (mcg/cm$^2$) | sd | sd |
|---|---|---|---|---|
| 0 | 0.014 | 0.06 | 0.002 | 0.02 |
| 1.5 | 0.13 | 0.19 | 0.02 | 0.014 |
| 3 | 0.28 | 0.37 | 0.19 | 0.04 |
| 5 | 0.32 | 0.52 | 0.20 | 0.13 |
| 7 | 0.33 | 0.54 | 0.18 | 0.16 |

Example 4

Fentanyl Base Loading of Thicker Silver Containing Claymat Patches

The patches were cut into definite size. They were weighed and immersed in 10 mg/ml Fentanyl base solution (5 ml) in a well-sealed container and allowed to equilibrate for 24 hours. The patches were washed using methanol to get rid of the surface drug completely. The patches were then dissolved in water, centrifuged and the supernatant was collected. The supernatant was filtered through 0.22-micron filler, and then the amount of fentanyl in the sample was quantitated. The amounts of fentanyl base released into the solution were provided in Table 5 and 6.

TABLE 5

The amount of drug loaded in thicker Fentanyl loaded silver containing claymat patches

| Product code | Fentanyl base per unit weight (mcg/mg) | Fentanyl base per unit area (mcg/cm$^2$) |
|---|---|---|
| MMI-1440 (80-micron thick patch) | 0.28 ± 0.06 | 8.35 ± 2.18 |

Examples 5

Drug Release Studies

The films were immersed in 4 ml methanol. 200 microliters of methanol were sampled at each time point, and the reservoir was replaced with same volume each time. The amount of drug in methanol was quantitated by HPLC.

TABLE 6

Drug release data of the thicker fentanyl loaded silver containing claymat patch (mcg = microgram)

| Time (h) | Cumulative release per unit weight (mcg/mg) | Cumulative release per unit area (mcg/sq cm) |
|---|---|---|
| 0 | 0.004 ± 0.001 | 0.11 ± 0.02 |
| 1.5 | 0.15 ± 0.06 | 4.63 ± 1.91 |
| 3 | 0.25 ± 0.03 | 7.48 ± 1.23 |
| 5 | 0.24 ± 0.06 | 7.35 ± 2.27 |

The 80-micrometer thick silver containing claymat samples were loaded with fentanyl base using the same method described in example 2. The load per unit weight did not change much. The load per surface area were doubled due to increase in the thickness from 40 microns to 80 microns. The equilibration of Fentanyl base loaded silver containing claymat patches in fentanyl base solution yield patches with a maximum fentanyl base loading of 8 mcg/sq·cm. The fentanyl base loading process was modified in order to increase the loading level of fentanyl base. In the modified process Fentanyl base loaded silver containing claymat patches were first wetted with fentanyl base solution in methanol. The solvent was evaporated under ambient conditions to form dry fentanyl base-loaded silver containing claymats. Using this modified method, fentanyl base loading levels as high as 80 mcg/cm$^2$ has been achieved.

Example 6

In Vitro Fentanyl Base Permeation Testing on Human Skin 80 mcg/cm$^2$ Fentanyl Loaded Silver Containing Claymat Patch Since the fentanyl base permeation from the 8 mcg/cm$^2$ Fentanyl loaded silver containing claymat patches resulted in the very low amount of fentanyl base diffusion through the human skin, we decided to treat Fentanyl loaded silver containing claymat patches with 10×higher loading of fentanyl base. The data of higher fentanyl base-loaded Fentanyl loaded silver containing claymat patch is provided in Table 7.

TABLE 7

Loading amount of fentanyl base in Fentanyl loaded silver containing claymat used in Human Skin Permeation Testing

| Product code | Fentanyl base per unit area (microgram per sq. cm) |
| --- | --- |
| 1440 (80-100 micron thickness) | 84.54 ± 11.14 |

Drug Permeation Studies

Method: The drug loaded Fentanyl loaded silver containing claymat patch was placed on the backing film with an adhesive. The drug transport of drug from the Fentanyl loaded silver containing claymat patch across the microtomed human cadaver skin (0.25 mm) was performed using Franz diffusion cell set up. The patch was overlaid on the human skin with clay patch facing the epidermis side of the skin placed on a rubber ring. The skin samples were previously tested for integrity by using electrical resistivity equipment and Transepidermal water loss (Delfin Technologies) equipment. The second rubber ring was placed on the patch and mounted on the Fran diffusion cell. The receiver compartment was filled with pH 7.4 buffer. The receiver compartment fluid was withdrawn at 2 hours interval and analyzed for Fentanyl base content by HPLC.

Figure 4:
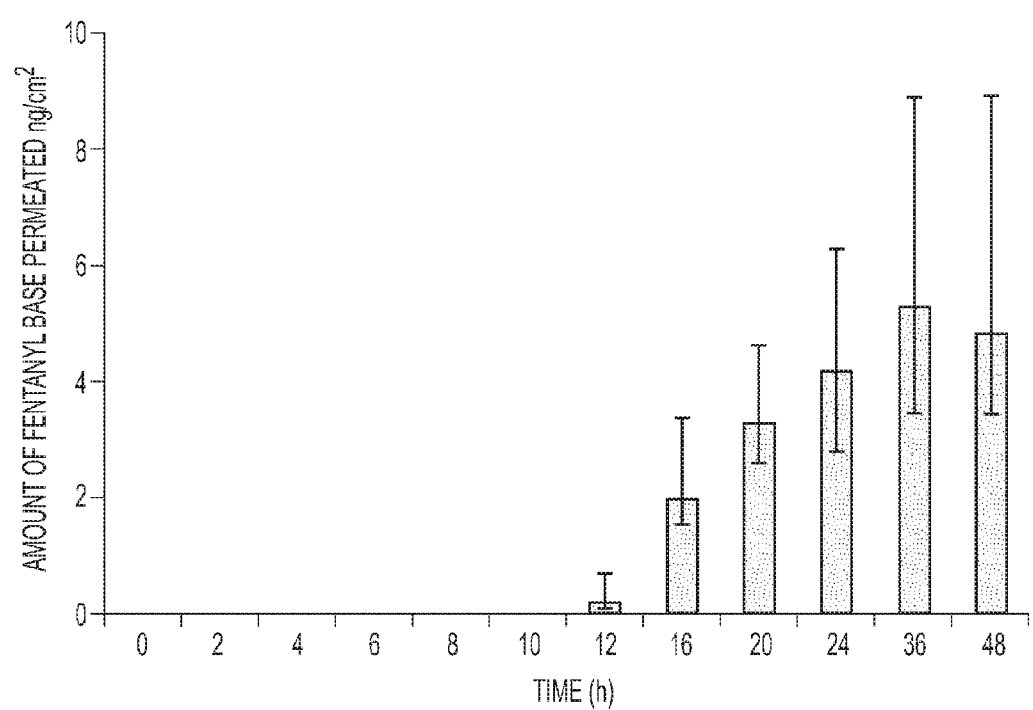
FIG. 4 provides the amount of fentanyl (nanogram per sq·cm) permeated across the cadaver skin from the multi-functional claymat patch loaded with 80 micrograms per sq·cm of fentanyl.

Results: The permeation across the skin was found to have a lag time 16 h. After 12 hours, the drug was detectable in the receiver compartment. The amount of fentanyl base (ng/sq·cm) permeated across the cadaver skin from the clay patch loaded with 80 micrograms per square cm per patch is provided in FIG. 4. As seen in FIG. 4, about 0.2 nanograms per square centimeter of fentanyl base was found to have permeated after about 12 h, about 1.9 nanograms per square centimeter of fentanyl base was found to have permeated after about 16 h, about 3.6 nanograms per square centimeter of fentanyl base was found to have permeated after about 20 hours, about 4.1 nanograms per square centimeter of fentanyl base was found to have permeated after about 24 hours, about 5.1 nanograms per square centimeter of fentanyl base was found to have permeated after about 36 hours, and about 4.9 nanograms per square centimeter of fentanyl base was found to have permeated after about 48 hours.

Drug Penetration Studies

Method: The set up was similar that set up for skin permeation studies. However, in this study, the skin was removed at different time points, the active diffusion area of the skin was biopsy punched, the surface was washed with water 3 times and wiped with a kimwipe. The skin was dissolved in 1N sodium hydroxide by incubating overnight. The sodium hydroxide solution was centrifuged alter overnight incubation; 1N perchloric acid was incorporated to precipitate the proteins. The mixture was centrifuged again, and the supernatant was diluted (1:1) with phosphate buffer and injected into HPLC for quantitation. Three trials were run for each time point for 8 hours.

Figure 5:
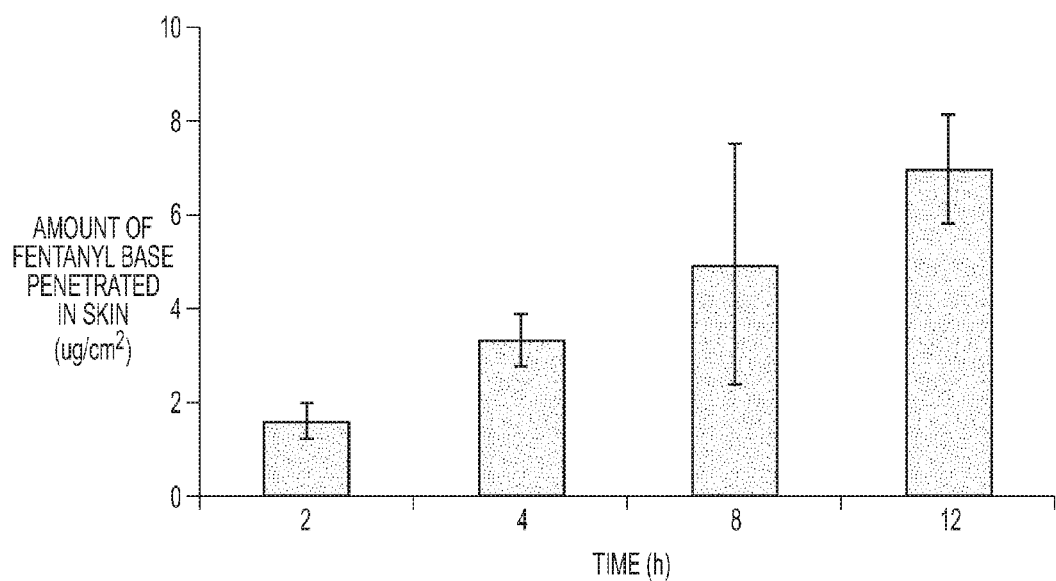
FIG. 5 provides the amount of fentanyl (microgram per sq·cm) penetrated in the skin after different time points FIGS. 6A and 6B provide hot plate testing with 80 micrograms per sq·cm Fentanyl loaded silver containing claymat patches: Antinociception action of fentanyl delivered topically from Fentanyl loaded silver containing claymat.

Results: The cumulative amount of drug penetrated into the skin increased with time is provided in FIG. 5. The amount of drug after 2 hours and 4 hours was about 1.53 and 3.30 mcg/sq·cm respectively (FIG. 5). The amount of drug in 8th hour and 12th hour were 4.90 and 6.92 mcg/cm$^2$ respectively.

Example 7

After in-vitro optimization of the analgesic delivery from fentanyl base loaded silver containing claymat, the prototype topical dressing was tested with an animal (rat) pain model (Hot plate test). Pain response in animals can be measured with the hot plate test. This test can also be used to test the efficacy of analgesics by observing the reaction to pain caused by heat. The main behavioral reaction to heat-induced pain in rats in this system is licking of the hind paws (in response to moderate heat, 48.5 degree C.). The delay in time before a rat exhibits this behavior after exposure to heat is labeled as the paw withdrawal latency (PWL). A higher PWL value indicates less pain (or increased delay of pain) felt by the animal.

Figure 6A:
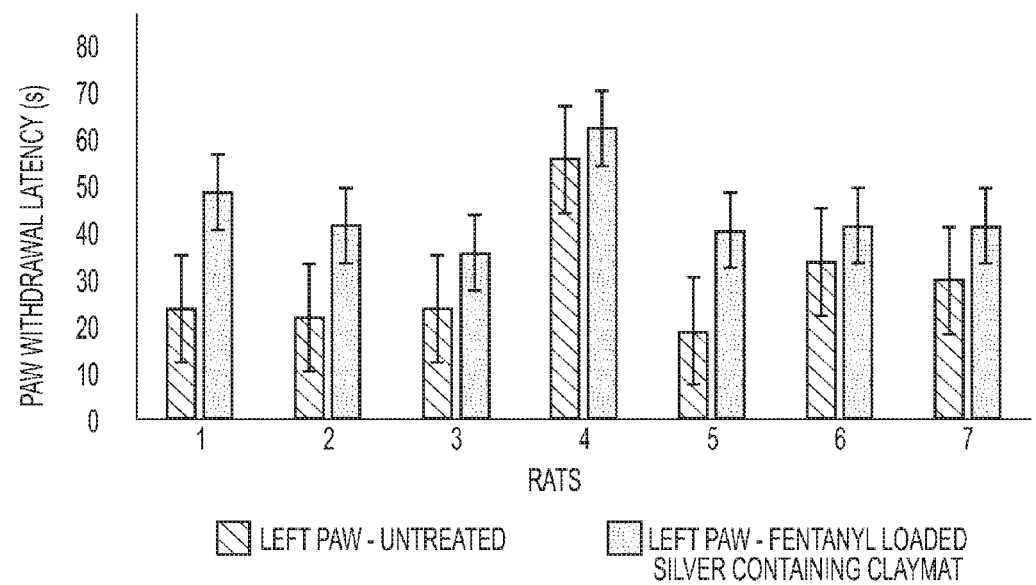
FIG. 6A shows that fentanyl increased the paw withdrawal latencies in left hind paw compared to left paw of the untreated rat.
Figure 6B:
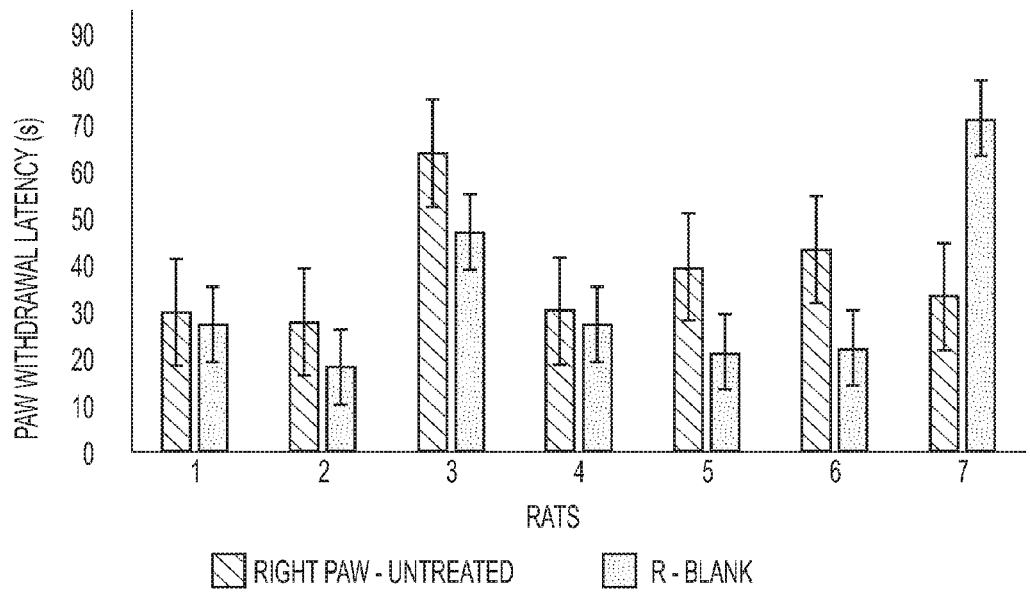
FIG. 6B shows that right hind paw treated with a silver containing claymat patch labeled as "R-blank" showed a decrease in the paw withdrawal latencies as compared to the untreated sight hind paw of the animal.

The test equipment consists of a thermo-regulated hot plate upon which a glass enclosure was placed to keep the rat over the heated surface. The rat was placed on the hot plate and the percentage of time the animal stayed on the hot plate was measured. The animal was able to stay for a longer duration due to the local anesthetic action of fentanyl base. Male, 8 weeks old Sprague-Dawley Rats were purchased from Harlan Laboratories (South Easton, Mass.). Fentanyl base loaded silver containing claymat patch (80 micrograms per square centimeter fentanyl base concentration) was placed on the plantar aspect of the left hind foot (test limb) and blank silver containing claymat (no fentanyl base) referred as 'R-blank'' in FIG. 6B was placed on the plantar aspect of the right hind foot (control hind limb) of the same rat. The patches were secured to the hind limbs using an adhesive backing film. After 12 hours exposure time, both patches were removed, and after 30 minutes the rat was subjected to hot plate analgesia testing using a hot plate analgesia meter (HTC Life Science Inc., Woodland. Hill, Calif.). Hot plate analgesia tests were carried out at 48.5 degree C. Each test was recorded using a hand-held video camera. Video footages were analyzed to determine the paw withdrawal time (PWL, the time it took for the rat to lift and start licking its control or test limb) for each hind paw. The paw withdrawal latency (PWL) values are plotted in FIG. 6A and FIG. 6B. We observed a ~111 percent increase in the PWL for Fentanyl loaded silver containing claymat-treated rat compared to an untreated animal. It should also be noted that the blank Silver containing claymat patch (R-blank) without the fentanyl base exhibited, a ~25 percent decrease in PWL values. The reason for this behavior could be the result of silver in the patch, coating the hind paw surface and making the skin more conductive to heat. Interestingly, a longer latency was observed with Fentanyl loaded silver containing claymat patch despite the fact that silver increases thermal conductivity, making the argument even stronger that local delivery of Fentanyl base works as an analgesic. Anomalous data in Rat #7 could be due to the uncertainty in the application of the patch because the patch was chewed off by the animal.

Example 8

Antimicrobial Testing of Fentanyl Loaded Silver Containing Claymat Samples

Kirby-Bauer agar diffusion assay for the following samples was conducted using four strains *E. coli, Salmonella Typhimurium, Staphylococcus aureus*, and *Streptococcus pyogenes*.

(a) Positive control (Amoxicillin/clavulanic acid—30 ug—BBL sensidisc Product number 231628).

Figure 7:
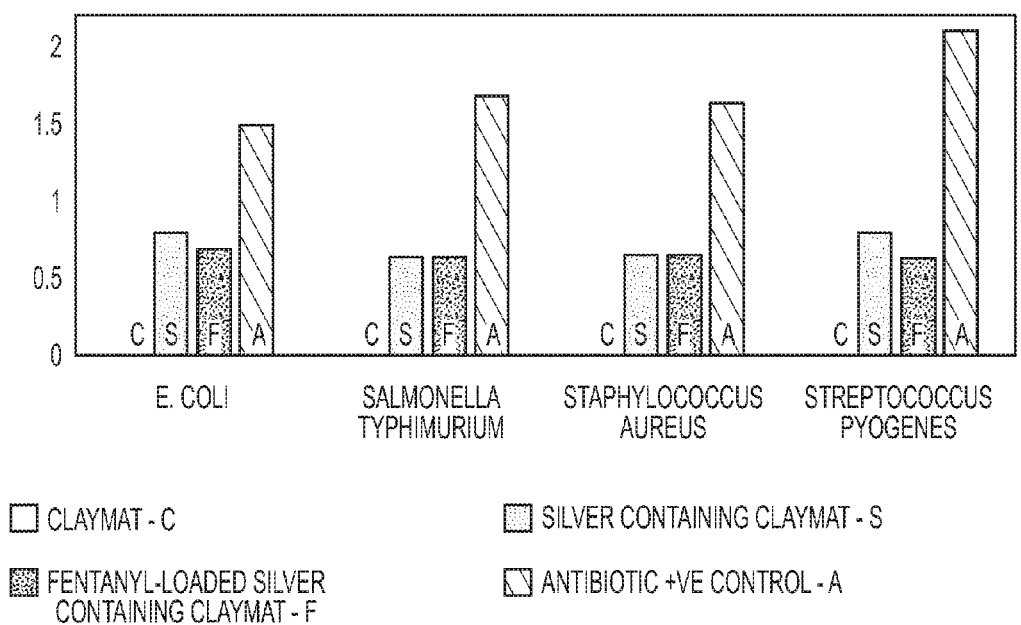
FIG. 7 provides Kirby-Bauer agar diffusion assay of silver containing claymat (S), Fentanyl-loaded Silver containing claymat (F) and pristine claymat (C) samples along with a positive control (A).

(b) Pristine montmorillonite clay (c) Silver containing montmorillonite clay and (d) Fentanyl-loaded silver containing montmorillonite clay The zone of inhibition values in centimeters are provided in Table 8, and the data is plotted in FIG. 7.

TABLE 8

Table for zone of inhibition

| | | | Zone of inhibition (cm) | | |
|---|---|---|---|---|---|
| Bacteria | Number of Replicates | Antibiotic + Control | Claymat (No silver added) | Silver-loaded clay (Silver containing claymat) | Fentanyl-loaded Silver containing claymat |
| E. coli | 1 | 1.5 | 0 | 0.7 | 0.8 |
| | 2 | 1.5 | 0 | 0.8 | 0.7 |
| | 3 | 1.5 | 0 | 0.9 | 0.6 |
| Salmonella Typhimurium | 1 | 1.9 | 0 | 0.6 | 0.6 |
| | 2 | 1.8 | 0 | 0.6 | 0.6 |
| | 3 | 2.1 | 0 | 0.7 | 0.5 |
| Staphylococcus aureus | 1 | 1.5 | 0 | 0.6 | 0.8 |
| | 2 | 1.5 | 0 | 0.7 | 0.7 |
| | 3 | 1.6 | 0 | 0.7 | 0.6 |
| Streptococcus pyogenes | 1 | 2.1 | 0 | 0.9 | 0.7 |
| | 2 | 2.2 | 0 | 0.8 | 0.6 |
| | 3 | 2 | 0 | 0.7 | 0.6 |

The positive control, silver containing montmorillonite claymat and fentanyl loaded silver containing montmorillonite claymat samples exhibited a zone of inhibition for all 4 bacteria tested. Further, no significant difference was observed between silver containing montmorillonite claymat and fentanyl loaded silver containing montmorillonite claymat samples. This has clearly demonstrated that fentanyl-loading did not affect the antimicrobial action of silver ion detrimentally. FIG. 7 shows the plot of zones of inhibition on claymat C, silver containing claymat S, fentanyl-loaded silver containing claymat F, and antibiotic positive (+ve) control A, when tested with *E. coli, Salmonella typhimurium, Staphylococcus aureus* and *Streptococcus pyogenes*.

Example 9

Synthesis of Lidocaine Base

In a typical synthesis, 10 g of lidocaine hydrochloride was dissolved in 50 mL of acetonitrile. Then 14 g of potassium carbonate was added and stirred at 50 degree C. for 1 h. Then the reaction mixture was filtered using a Buchner funnel and the filtrate was rotoevaporated to yield Lidocaine Base product in >95 percent yield. Silver containing claymats and plain claymats were loaded with lidocaine base, and their drug release study was conducted.

Example 10

Mixtures of silver nitrate and montmorillonite claymats were prepared, centrifuged, and washed following the same procedure as described in example 1 with different compositions as listed in the table below. After centrifugation and washing, various concentrations of lidocaine base and betaine were added to each mixture in a plastic bottle as shown in Table 9.

TABLE 9

Various compositions of claymat precursor solution

| Lidocaine base Concentration (weight percent) | Betaine Concentration (weight percent) | Total Mass of Solution (g) | Clay (g) | AgNO$_3$ (g) | Betaine (g) | Lidocaine base (g) |
|---|---|---|---|---|---|---|
| 7.5 | 15 | 120 | 6 | 0.612 | 0.9 | 0.45 |
| 7.5 | 20 | 120 | 6 | 0.612 | 1.2 | 0.45 |
| 7.5 | 25 | 120 | 6 | 0.612 | 1.5 | 0.45 |
| 7.5 | 30 | 120 | 6 | 0.612 | 1.8 | 0.45 |

All bottles were capped and placed in a ball mill overnight. After agitation on the ball mill, each bottled mixture was uncapped and placed in a desiccator with a vacuum pump attached to it to extract all the bubbles out of solution. Each dressing mixture was then poured onto a baking mat to dry. Clay mats were fully dried in 2-3 days. The area of the clay mat was approximated (368 square centimeters). Even though Lidocaine base concentration in the precursor solution was 7.5 weight percent the lidocaine base loading was about 1.2 milligram per square centimeter based on the size of the mat.

Example 11

Skin Penetration Studies

A 10×10 mm lidocaine base (5 milligrams per square centimeter) containing Silver containing claymat patch was secured onto the stratum corneum with the help of a backing membrane. The receptor compartment was filled with 5 mL of phosphate buffer (pH 7.4). The cells with skin and lidocaine hydrochloride patch were mounted on the diffusion apparatus. The receptor solution (Phosphate buffer saline pH 7.4) in contact with the underside of the skin was stirred magnetically at 600 rpm and its temperature maintained to achieve a skin surface temperature of 32.0±1.00 degree C. At time intervals of 0.5, 1, 1.5, 3 and 6 h clay patch was removed from the skin, the skin was washed with purified water, and tape stripped one time using 3M's adhesive tape to remove any adhering drug from the skin surface. The biopsy sample of the active diffusion area of the skin (0.64 square centimeters) was cut and subjected to extraction of lidocaine hydrochloride content for measurement.

Sample Analysis

Lidocaine base was extracted from skin that was cut into small pieces using 1 mL of water. The skin sample was vortexed with water for 10 min. These samples were kept for shaking for 1 hr and centrifuged for 15 min at 13000 rpm; the supernatant was subjected to analysis by HPLC.

Figure 8:
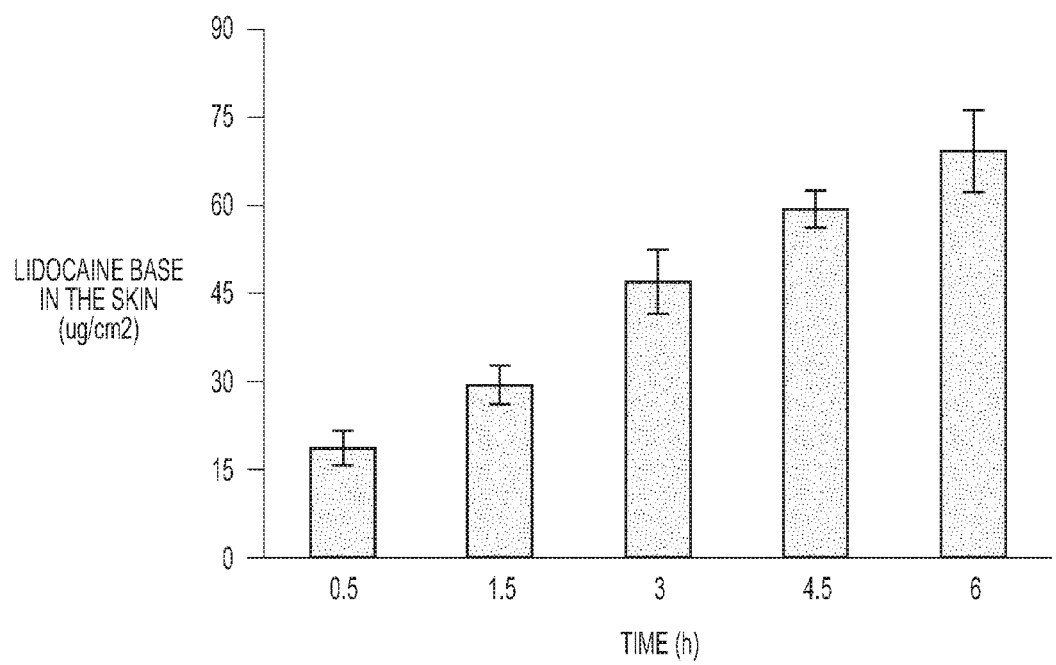
FIG. 8 provides the lidocaine base amounts in microgram per square centimeter detected on the skin as a function of time.

Results: There was an increasing trend in the amount of drug loaded into the skin with time. FIG. 8 shows that the total amount of drug loaded in the skin were about 18.7 micrograms per square centimeter in 0.5 h, about 29.5 micrograms per square centimeter in 1.5 h, about 47 micrograms per square centimeter in 3 h, about 59.6 micrograms per square centimeter in 4.5 h, and about 69 micrograms per square centimeter in 6 hours.

Evaluation of Antinociceptive Activity of Drug Loaded Clay Patches (Hot Plate Test)

Patch preparation: Plain patches of size 10×10 mm were cut and weighed. 20 microliter of 250 mg/mL (5 mg per square centimeter) of Lidocaine base solution in methanol was loaded carefully by adding dropwise using micropipette for each patch. Methanol was allowed to evaporate at room temperature. In one batch of patches, Fentanyl was also loaded similarly.

Grouping: Male Sprague dawley rats (250-300 g) were be used for the study. They were randomly grouped into four groups of four animals each as mentioned below:

Group I: Silver containing claymat patch only

Group II: Silver containing claymat patch loaded with Lidocaine base

Group III: Silver containing claymat patch loaded with Lidocaine base and Fentanyl Group IV: Clay/Betaine Patch loaded with Lidocaine Group V: Plain clay patch only Method: The animals were allowed for several days of acclimatization for handling. Two days prior to experimentation they were allowed acclimatize for baseline thermal latency. On the day of the experiment, the patches were applied on the plantar surface of the hind limbs. The patches were secured to the hind limbs using an adhesive bandage. After 6 hrs, the patches were removed, and the animals were subjected to hot plate analgesia, testing using a hot plate analgesia meter (HTC Life Science Inc., Woodland Hill, Calif.). Hot plate analgesia tests were carried out at 48.5 degree C. Each test was recorded using a hand-held video camera. Video footages were analyzed to determine the paw withdrawal time (PWL, the time it took for the rat to lift and start licking its control or test limb) for each hind paw. A cut-off period of 60 s was given to avoid any potential thermal injury to the rat's paw. A minimum of three replicates was run on each rat. The mean and SD was calculated for each group.

Figure 9:
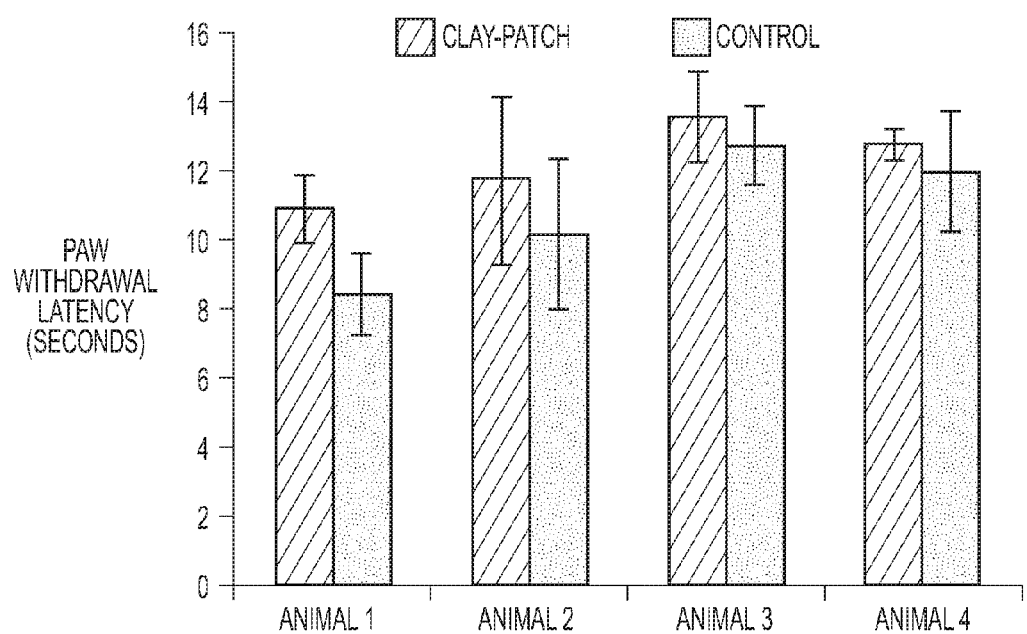
FIG. 9 provides the Paw Withdrawal Latency (PWL) of rats treated with pristine claymat (without out silver) patch and control without any patch applied on the plantar surface of the hind limbs.
Figure 10:
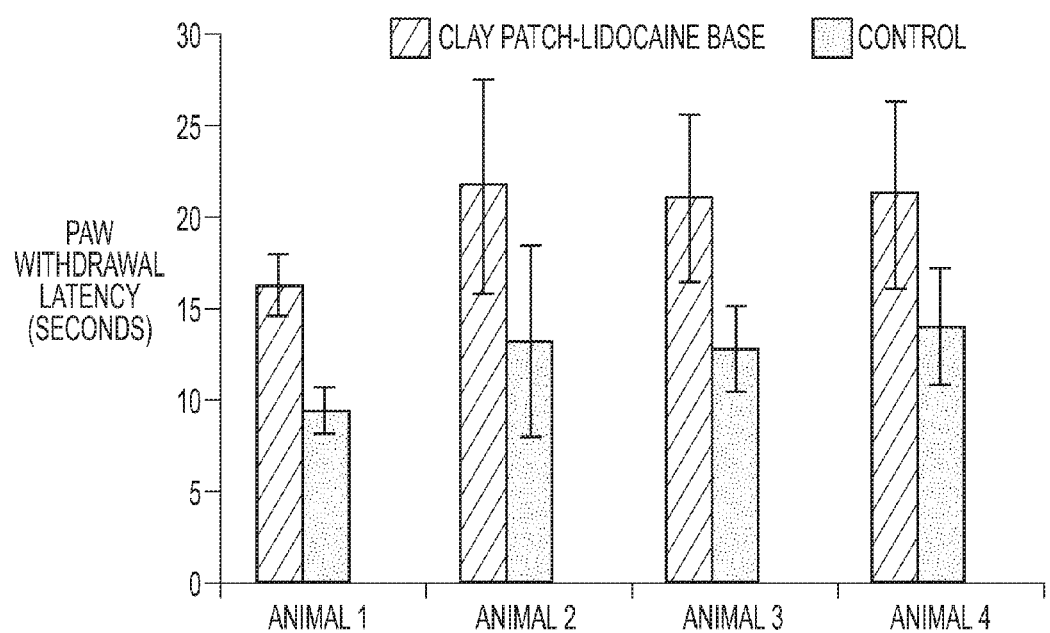
FIG. 10 provides the Paw Withdrawal latency (PWL) of rats treated with pristine claymat (without out silver) patch and lidocaine base loaded claymat patch applied on the plantar surface of the hind limbs.
Figure 11:
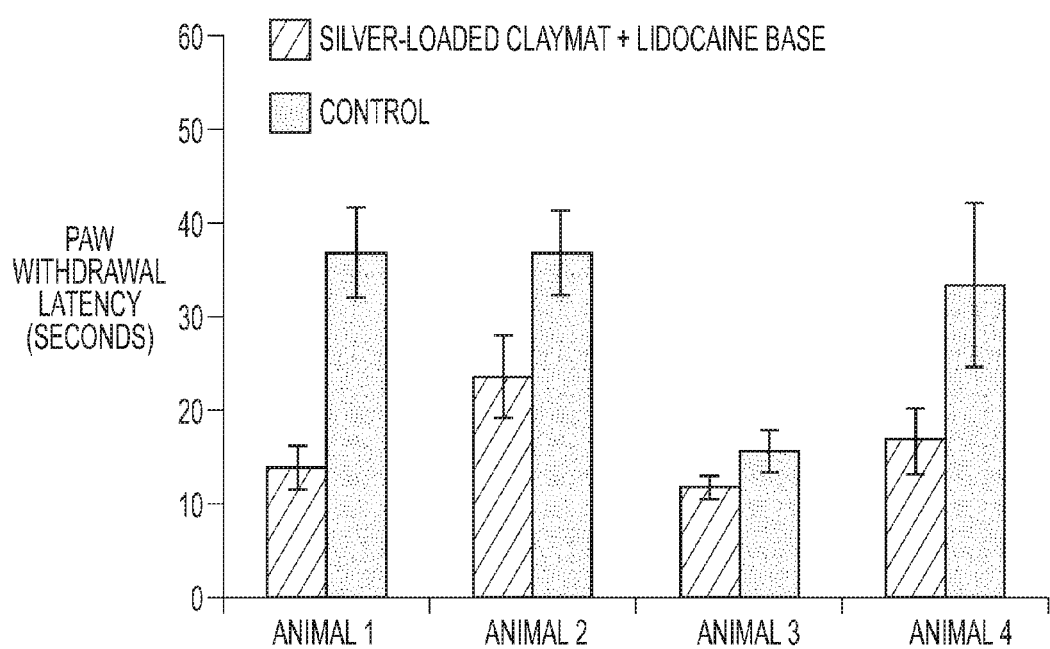
FIG. 11 provides the Paw Withdrawal latency (PWL) of rats treated with silver containing claymat patch and lidocaine base loaded silver containing claymat patch applied on the plantar surface of the hind limbs.
Figure 12:
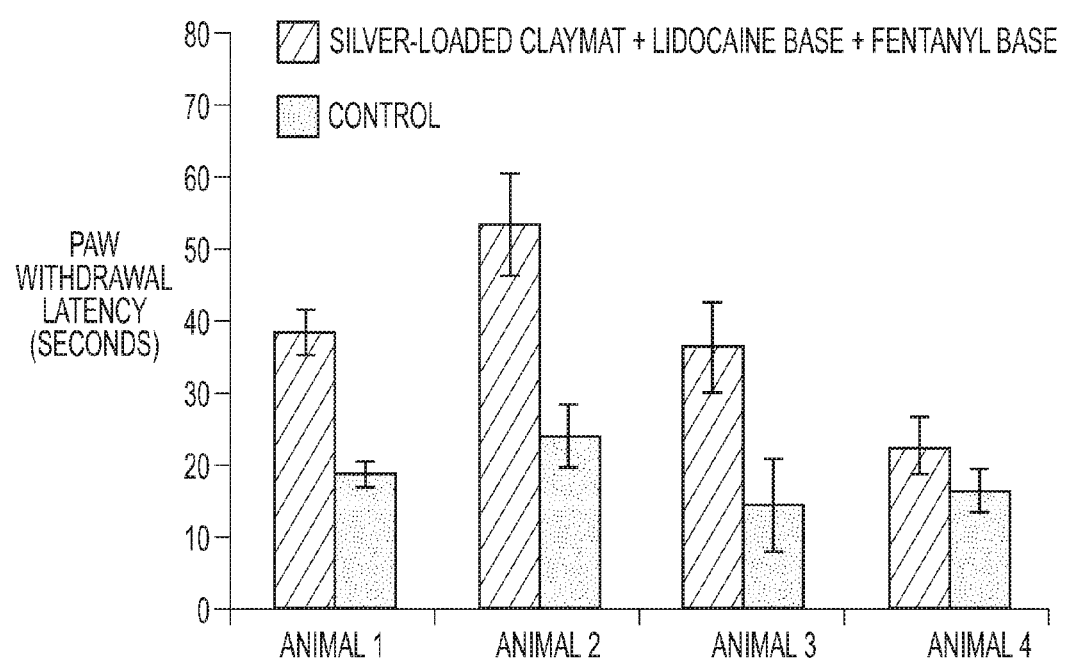
FIG. 12 provides the Paw Withdrawal Latency (PWL) of rats treated with silver containing claymat patch and a mixture of lidocaine base and fentanyl loaded silver containing claymat patch applied on the plantar surface of the hind limbs.

Results: The Paw Withdrawal Latency (PWL) data in seconds for test animals is plotted in FIG. 9, FIG. 10, FIG. 11 and FIG. 12. Paw Withdrawal Latency (PWL) of the plain Silver containing claymat patch applied rats was reduced by ~28 percent. Interestingly, the PWL data provided in FIG. 11 show that for the Silver containing claymat loaded with lidocaine base (Group II) was also reduced by ~52 percent. On the other side, in the case of plain clay patch, there was no significant increase in the PWL as shown in FIG. 9. However, in the case of clay patch loaded with lidocaine PWL increased by about 62 percent as shown in FIG. 10. From these two sets of data, it is evident that presence of silver in silver containing claymat increases the conductivity of the skin overcoming the local anesthetic effect of lidocaine. The PWL increased ~103 percent as anticipated in the silver containing claymat patch loaded with lidocaine base (5 mg/cm$^2$) and Fentanyl (1 mg/cm$^2$) as shown in FIG. 12 which was comparable to the positive control commercial lidocaine patch which resulted in an increase in the PWL ~96 percent.

What is claimed is:

1. A method of preparing a multifunctional polymer-free clay film comprising a clay, an antimicrobial agent, a zwitterion and an analgesic, the method comprising:
    a) mixing a clay, the antimicrobial agent and water to form a first slurry;
    b) centrifuging and washing the first slurry of step a) with water to obtain a washed second slurry;
    c) adding a zwitterion and water to the washed second slurry of step b) to obtain a third slurry;
    d) casting the third slurry of step c) onto a substrate to obtain a first dried product;
    e) adding drops of the analgesic in a non-aqueous solvent onto the first dried product of step d) to obtain a resultant product,
    f) drying the resultant product to obtain a second dried product; and,
    g) separating the second dried product of step f) from the substrate of step d), wherein the second dried product of steps f) and g) is the multifunctional polymer-free clay film which provides both antimicrobial and pain relieving properties, wherein the zwitterion is selected from the group consisting of N,N,N-trimethylglycine and N,N,N-trimethylglycine hydrochloride, and wherein the antimicrobial agent in the multifunctional polymer-free clay film is selected from the group consisting of silver ion, copper, silver-containing compounds, and, copper containing compounds.

2. The method of claim 1, wherein the silver-containing compound is silver nitrate.

3. The method of claim 1, wherein the analgesic is selected from the group consisting of
    opioid analgesics, nonsteroidal anti-inflammatory drugs (NSAIDs), adjuvant analgesics, cannabinoids and combinations thereof,
    wherein the opioid analgesics are selected from the group consisting of Morphine, fentanyl, Buprenorphine, fentanyl base, and combinations thereof,
    wherein the adjuvant analgesics are selected from the group consisting of capsaicin, clonidine, ketamine, lidocaine base, loperamide base, and combinations thereof.

4. The method of claim 1, wherein the substrate is selected from the group consisting of a silicone sheet, a fabric, and a glass surface.

5. The method of claim 1, wherein the clay is selected from the group consisting of montmorillonite, kaolinite, smectite, and bentonite.

6. A multifunctional polymer-free clay film prepared by the method of claim 1, wherein the multifunctional polymer-free film provides both antimicrobial and pain relieving properties.

* * * * *